(12) United States Patent
Nguyen et al.

(10) Patent No.: US 6,412,340 B1
(45) Date of Patent: Jul. 2, 2002

(54) CELL DETECTION MECHANISM

(75) Inventors: Nick Ngoc Nguyen, Costa Mesa; Doug Truong, Santa Ana; Hal Williams, San Clemente, all of CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/500,182

(22) Filed: Feb. 7, 2000

(51) Int. Cl.⁷ .............................. G01B 5/28; A61L 2/00
(52) U.S. Cl. ............................ 73/104; 206/569; 141/1; 414/411; 414/416.03; 422/28; 422/292
(58) Field of Search ........................ 73/104, 105; 141/1; 206/569; 422/28, 292; 414/411, 416.03

(56) References Cited

U.S. PATENT DOCUMENTS

| | | | |
|---|---|---|---|
| 2,363,691 A | * 11/1944 | Reason | 73/105 |
| 3,283,568 A | * 11/1966 | Reason | 73/105 |
| 3,741,054 A | 6/1973 | Alperin et al. | 83/80 |
| 4,643,876 A | 2/1987 | Jacobs et al. | |
| 4,756,882 A | 7/1988 | Jacobs et al. | |
| 4,817,800 A | 4/1989 | Williams et al. | |
| 4,869,286 A | 9/1989 | Williams et al. | |
| 4,909,287 A | 3/1990 | Williams et al. | |
| 4,913,196 A | 4/1990 | Williams et al. | |
| 4,938,262 A | 7/1990 | Williams et al. | |
| 4,941,518 A | 7/1990 | Williams et al. | |
| 5,656,238 A | 8/1997 | Spencer et al. | |
| 5,882,611 A | 3/1999 | Williams et al. | |
| 5,887,716 A | 3/1999 | Williams et al. | |

FOREIGN PATENT DOCUMENTS

FR    2 677 116    6/1991    .................. 33/551

* cited by examiner

*Primary Examiner*—Daniel S. Larkin
(74) *Attorney, Agent, or Firm*—Knobbe, Martens, Olson & Bear, LLP

(57) ABSTRACT

A cassette sensing mechanism and a method for detecting the unevenness of a surface by detecting the difference between two paths on the surface. The mechanism contains two pawls connected to a connector at one end. The second end of one pawl contacts a portion of one path on the surface, and the second end of the other pawl contacts a portion of the other path on the surface. One path is smooth, and the other path contains grooves. A sensor on one pawl senses the relative position of the other pawl. The unevenness of the surface can be detected by monitoring the relative positions of the two pawls as the two pawls travel along the two paths. The sensing mechanism may be used for monitoring the position on a cassette in a sterilization system.

39 Claims, 18 Drawing Sheets

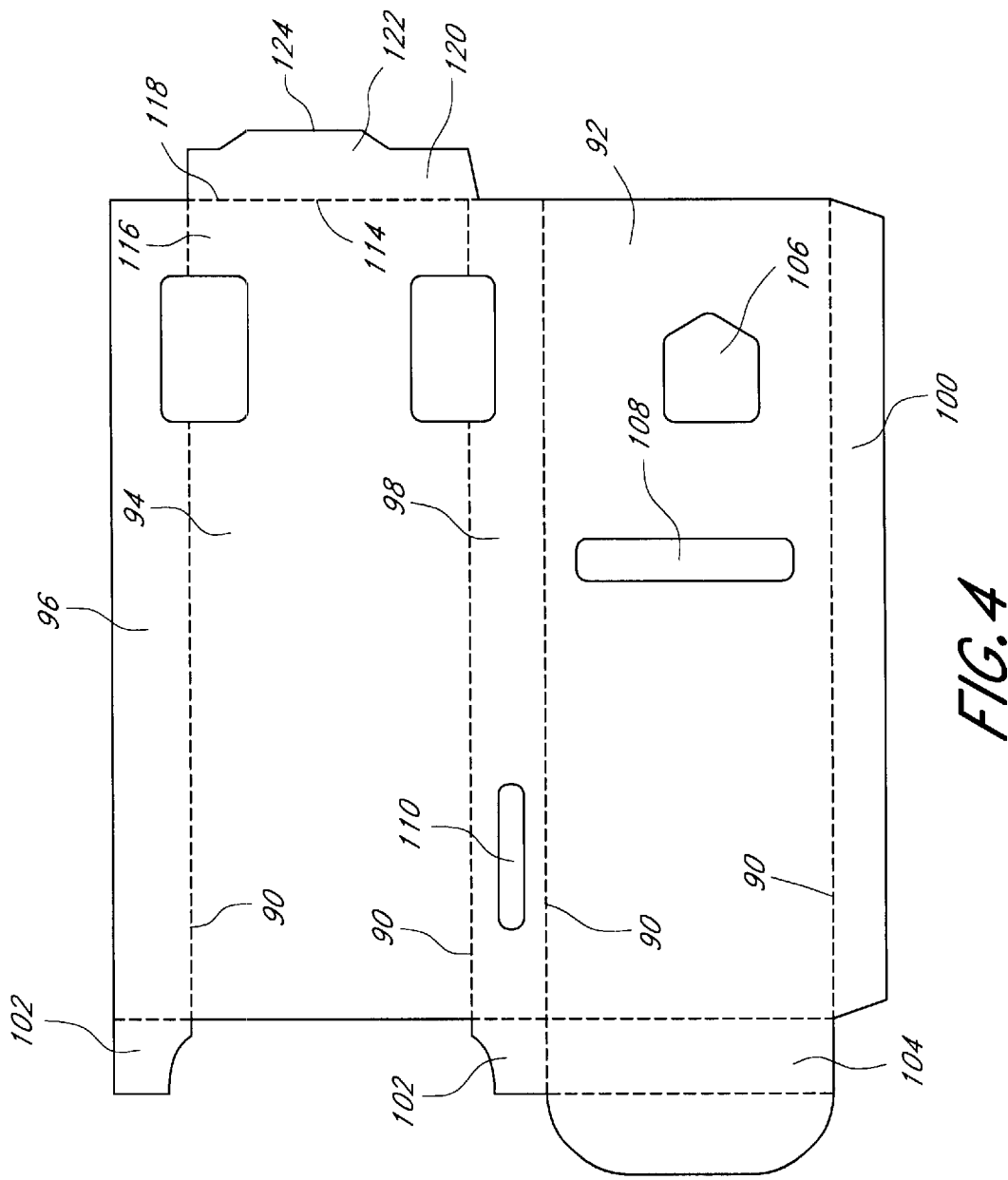

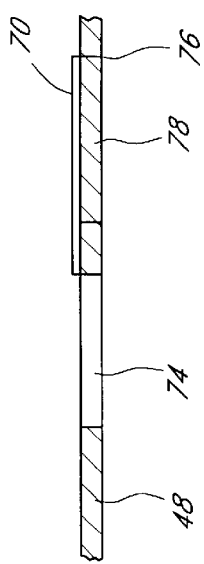
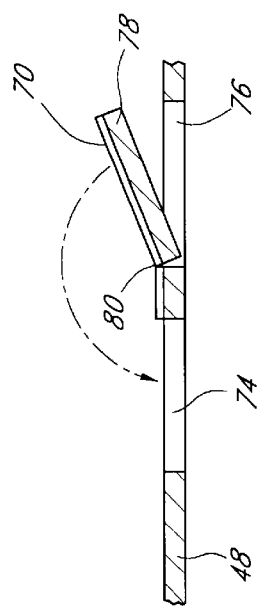
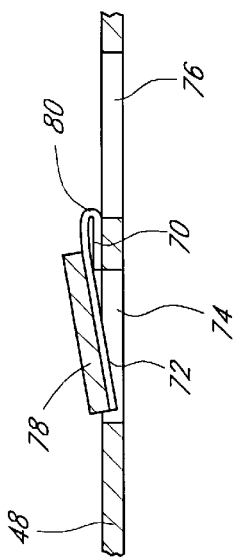
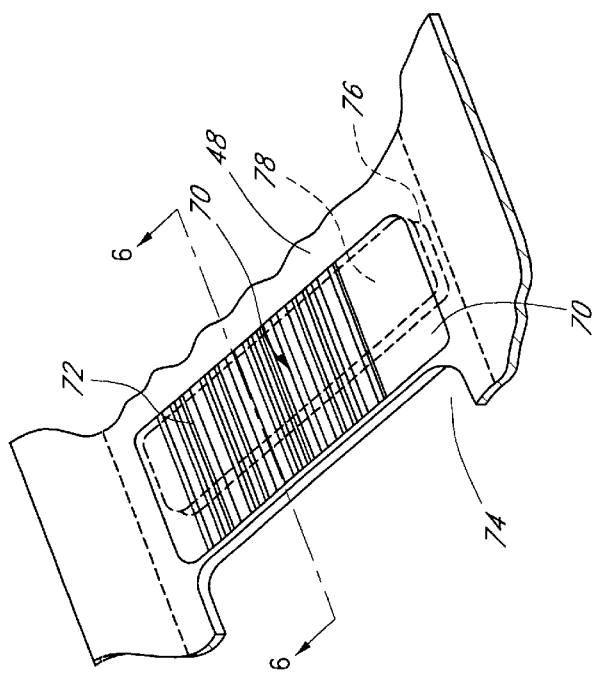

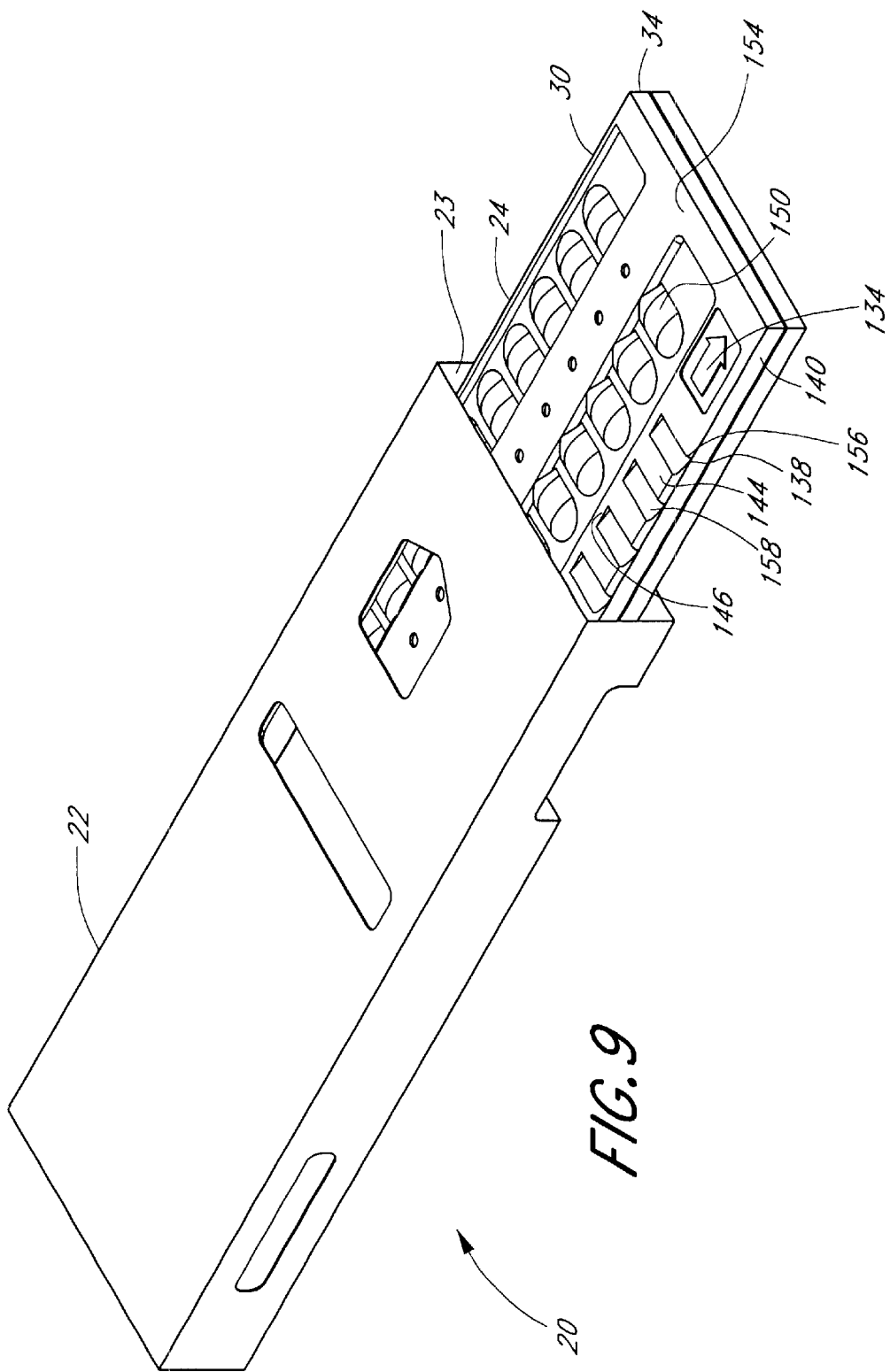

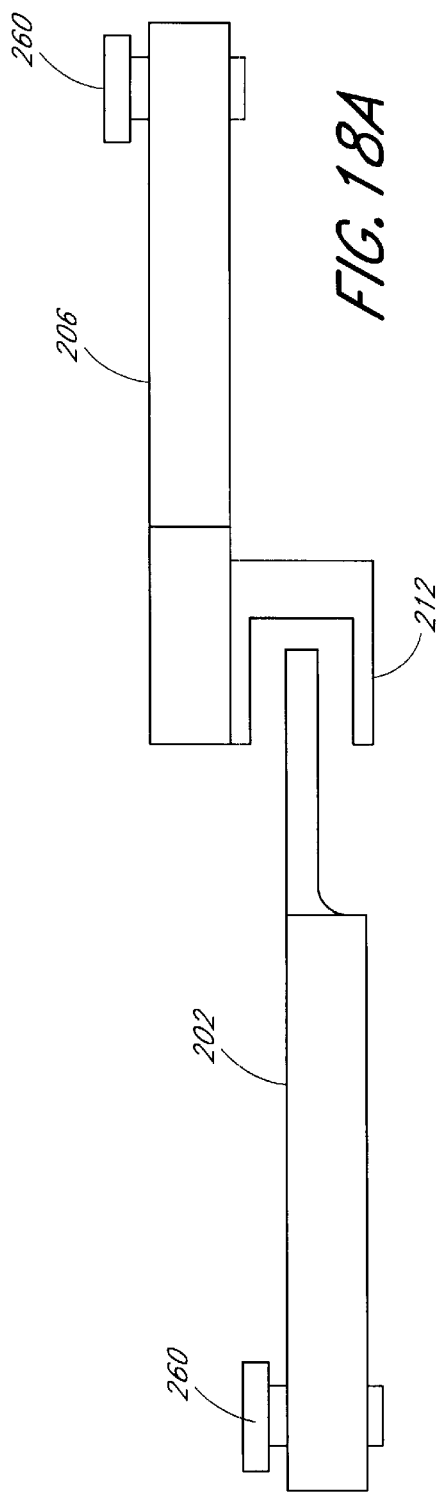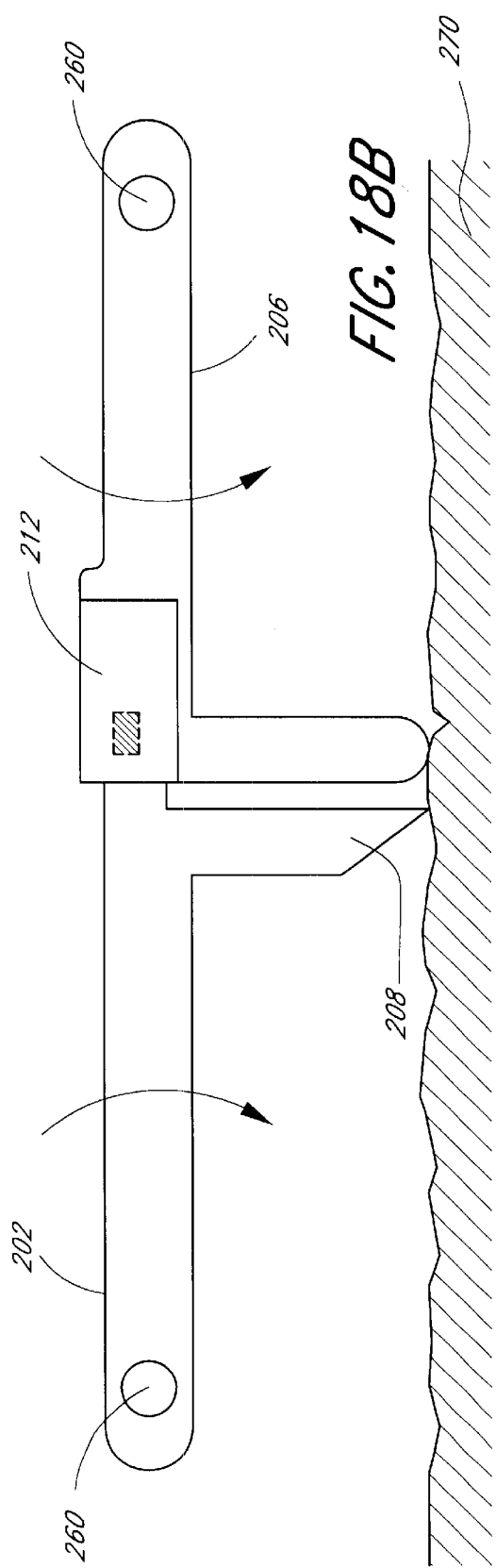

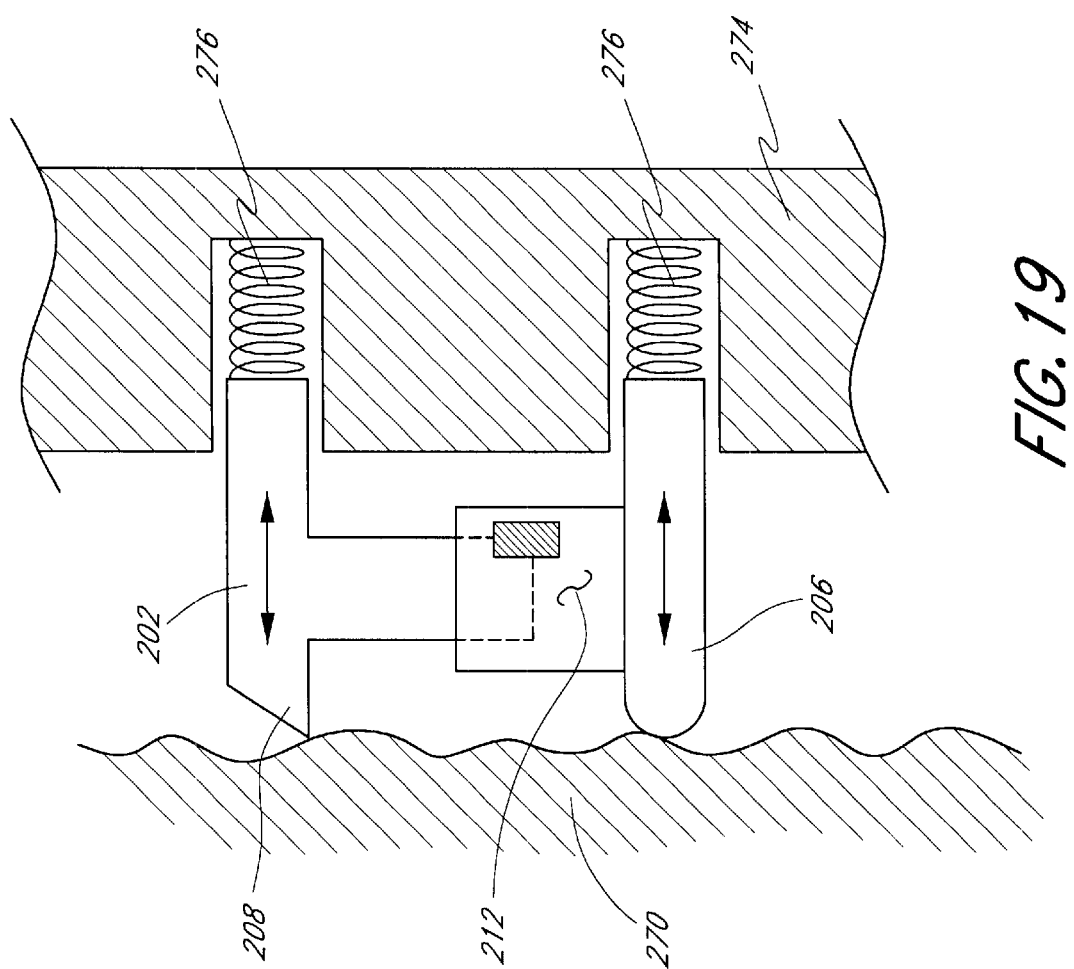

CELL DETECTION MECHANISM

BACKGROUND OF THE INVENTION

1. Field of the Invention

This invention relates to an apparatus and a method for sensing the position of a device on a cassette, more particularly for sensing the position of the cassette handling apparatus on a cassette holding liquid sterilant.

2. Description of the Related Art

U.S. Pat. No. 4,643,876, incorporated herein by reference, discloses a sterilization system in which a vaporizable germicide, such as hydrogen peroxide, is introduced into an evacuated sterilization chamber. The vaporizable germicide vaporizes and is allowed to disperse throughout the chamber and onto the items to be sterilized. After a desired period of time electrical energy is applied to an electrode to form a plasma to complete the sterilization cycle.

This system has been successfully commercialized as the STERRAD® Sterilization System and is available from Advanced Sterilization Products, a Division of Ethicon, Inc., Irvine, Calif. The system is used in hospitals and other environments where it is operated repeatedly throughout the day by personnel having a widely varying range of understanding of the apparatus. In order to insure safeguards in the event of operator error, the system employs an automated delivery system for delivering the liquid vaporizable germicide to the sterilization chamber. Measured portions of the liquid germicide, for example hydrogen peroxide, are provided in rupturable cells within a rigid cassette housing. The cassette and operation of the delivery system are more fully described in the Williams et al. patents, U.S. Pat. No. 4,817,800 issued Apr. 4, 1989; U.S. Pat. No. 4,913,196 issued Apr. 3, 1990; U.S. Pat. No. 4,938,262 issued Jul. 3, 1990; and U.S. Pat. No. 4,941,518 issued Jul. 17, 1990, all of which are incorporated herein by reference. In the above-referenced patents, the operator manually grasps the cassette housing and inserts it into the sterilizer. When spent, the cassette is ejected.

Prior methods of sterilization utilized heat, steam, or toxic, flammable chemicals, such as ethylene oxide. Heat or steam can damage delicate medical equipment. Use of toxic chemicals for sterilization poses risks to workers. Sterilization of equipment with hydrogen peroxide and plasma with the cassette system provide many advantages over the prior sterilization systems. The hydrogen peroxide and plasma kill a wide range of bacteria, viruses, and spores at low temperatures, minimizing the chance of damaging delicate temperature-sensitive instruments. Further, hydrogen peroxide decomposes to water and oxygen after exposure to plasma, avoiding the need to dispose of any toxic byproducts. Finally, the cassette isolates the operator from the liquid hydrogen peroxide in the cells in the cassette.

U.S. Pat. No. 5,882,611 issued Mar. 16, 1999 and U.S. Pat. No. 5,887,716 issued Mar. 30, 1999 to Williams et al., herein incorporated by reference, describe an improved cassette and delivery system, in which the cassette is encased in a protective sleeve. The sleeve isolates the cassette from the operator's hands during all stages of handling and absorbs any drops of liquid hydrogen peroxide which might be left on the exterior of the spent cassette, protecting the operator from contact with any sterilant which escapes from the cassette. The delivery system automatically extracts the cassette from the sleeve, delivers the liquid germicide to the sterilization chamber, and reinserts the spent cassette into the sleeve, all without any handling by the operator. Further, the delivery system checks the cassette before processing to insure that the cassette is not already used or that the cassette is expired.

Although the delivery system described in U.S. Pat. No. 5,882,611 offers many advantages over the previous delivery systems, opportunities for improvement remain. The delivery system is complex and expensive. Further, the delivery system depends on a timer to determine which cell is in the injector rather than directly sensing the position of the cassette in the delivery system.

There is thus a need for a delivery system which is simpler and less expensive than the previously described systems while retaining the advantage of minimizing operator handling. Further, there is a need for a delivery system in which the position of the delivery system and injection system on the cassette may be determined with more certainty than simply relying on a timer.

The cassette sensing mechanism and delivery system of the present invention provide a positive indication of the location of the cassette in the delivery and injection system. Further, the delivery system is far less complex than the previous delivery system. Finally, the delivery system of the present invention retains the advantages of the prior delivery and injection system in extracting the cassette from a sleeve, delivering the liquid sterilant to the sterilization chamber, and reinserting the spent cassette into the sleeve without the requirement for operator intervention.

SUMMARY OF THE INVENTION

One aspect of the invention involves a sensing mechanism for detecting the unevenness of a surface on a device, where there is at least a first path and a second path on the surface. The sensing mechanism contains at least one connector, a first pawl, a second pawl, and a sensor mounted on the first pawl or the second pawl. The first end of the first pawl is connected to the connector in a manner allowing movement of the first pawl and the second end of the first pawl contacts a portion of the first path on the surface. The first end of the second pawl is connected to the connector in a manner allowing movement of the second pawl and the second end of the second pawl contacts a portion of the second path. The sensor detects the position of the first pawl relative to the second pawl.

Advantageously, the first path and said second path are noncoincident. Preferably, the device is a cassette. In an embodiment, the cassette contains germnicide. Advantageously, the germicide contains hydrogen peroxide. Preferably, the connector is a pivot, where the first pawl and said second pawl rotate about the pivot. Advantageously, the movement of the first pawl and the second pawl is due to gravity. In another embodiment, the movement of the first pawl and the second pawl is due to one or more springs.

The unevenness of the surface may be on the top, bottom, or side of the device. The sensor may be a photoelectric sensor, an electromechanical sensor, or a proximity sensor. Advantageously, the first path is adjacent to second path. Preferably, the mechanism also contains a control unit.

Another aspect of the invention involves a sensing mechanism for detecting the position of a cassette having a first path and a second path, where the first path has at least one groove and the second path is relatively smooth. The mechanism includes at least one connector, a first pawl, a second pawl, and a sensor mounted on the first pawl or the second pawl. The first end of the first pawl is connected to the connector in a manner allowing movement of the first pawl and the second end of the first pawl contacts a portion of the first path on the surface. The first end of the second pawl is connected to the connector in a manner allowing movement of the second pawl, while the second end of the second pawl contacts a portion of the said second path. The sensor detects the position of the first pawl relative to the second pawl, to detect the position of the cassette.

Preferably, the cassette contains germicide. Advantageously, the germicide is hydrogen peroxide. Preferably, the connector is a pivot, where the first pawl and said second pawl rotate about the pivot. In an embodiment, the movement of the pawls is due to gravity. In another embodiment, the movement of the pawls is due to a moving mechanism, such as a hydraulic mechanism, pneumatic mechanism, or one or more springs.

Another aspect of the invention involves a method for positioning a cassette for injection of germicide to a sterilization system. The method includes providing a cassette with a surface having a first path and a second path, where the first path has at least one groove and the second path is relatively smooth. The method also includes providing a sensing mechanism having at least one connector, two pawls connected to the connector in a manner allowing movement of the pawls, and a sensor mounted on one of the pawls. The method also includes inserting the cassette into the sensing mechanism in the sterilization system. The end of one pawl contacts a portion of the first path on the surface of the cassette and the end of the other pawl contacts a portion of the second path on the surface of the cassette. The relative position of the two pawls is determined with the sensor, thereby determining the position of the end of the pawl on the first path on the surface of the cassette. The method also includes moving the cassette until the pawl contacts the groove in the first path on the surface of the cassette, positioning the cassette for injection of germicide into said sterilization system.

Advantageously, the determining and moving steps are repeated. Preferably, the cassette contains germicide. In an embodiment, the method also includes injecting the germicide into the sterilization system. Preferably, the sensor is a photoelectric sensor, an electromechanical sensor, or a proximity sensor. Advantageously, the first path and the second path are noncoincident. Preferably, the germicide is hydrogen peroxide.

BRIEF DESCRIPTION OF THE DRAWINGS

FIG. 4 is a plan view of an unfolded blank of an outer layer of FIG. 1;

FIG. 5 is a perspective view of an identifying label on the sleeve inner layer of FIG. 3;

FIG. 6 is a sectional view of the label of FIG. 5, shown in the retracted position;

FIG. 7 is a sectional view as in FIG. 6, showing the label in a transitional orientation;

FIG. 8 is a sectional view as in FIG. 6, showing the label in the exposed orientation where the label is viewable through an aperture;

FIG. 9 is a perspective view of a cassette assembly with the cassette partially removed from the sleeve;

FIG. 18A is a schematic top view of a portion of an embodiment of the cassette sensing mechanism in which the pawl and the pawl bracket are mounted on two different pivots;

FIG. 18B is a schematic side view of the cassette sensing mechanism of FIG. 18A;

FIG. 19 is a schematic side view of a portion of an embodiment of the cassette sensing mechanism in which the pawl and the pawl bracket are mounted on springs in a support, where the pawl and the pawl bracket move laterally rather than rotationally.

DETAILED DESCRIPTION OF THE PREFERRED EMBODIMENT

The apparatus of the present invention comprises a delivery system and a cassette sensing mechanism intended to extract a cassette from a cassette assembly, advance the cassette into a delivery system, sense the position of the cassette in the delivery system, make the cassette available to an injection system, advance the position of the cassette in the delivery system to make other portions of the cassette available to the injection system, repeat the operation until the cells in the cassette have been exhausted, insert the spent cassette back into the cassette assembly, and eject the spent cassette assembly from the delivery system. The cassette sensing mechanism provides a direct indication of the position of the delivery system on the cassette by sensing the variations in the height between the grooves and flat ridges on a grooved portion of a cassette as compared to an adjacent flat ridge on the cassette.

Although presented in the context of sensing mechanism for a cassette, it is to be understood that the apparatus has broad applicability and is not limited to sensing the position of a delivery apparatus on a cassette for sterilization. The cassette sensing mechanism can be used to determine variations in height or thickness of any device which has a portion with variable height or thickness in relatively close proximity to a portion with a constant height or thickness. The mechanism can also be used to compare heights of one portion of a device with an adjacent portion of a device, even where both portions vary. The apparatus of the present invention thus has broad applicability to a wide range of products and processes. For example, the apparatus can be applied to determining relative thickness of layers on semiconductors.

The cassette, cassette assembly, and an apparatus which was used to extract the cassette from the cassette assembly were described in U.S. Pat. No. 5,887,716. Although the cassette and cassette assembly are not part of the apparatus of the present invention, the apparatus and method of the present invention utilize the cassette and cassette assembly of U.S. Pat. No. 5,887,716, though other cassettes and cassette assemblies are suitable for use in the apparatus and the method. It is necessary to describe the cassette and cassette assembly in order to understand the apparatus and the method of the present invention. The cassette and cassette assembly will therefore be described before the apparatus and method of the present invention are described.

Cassette Assembly

Figure 1:
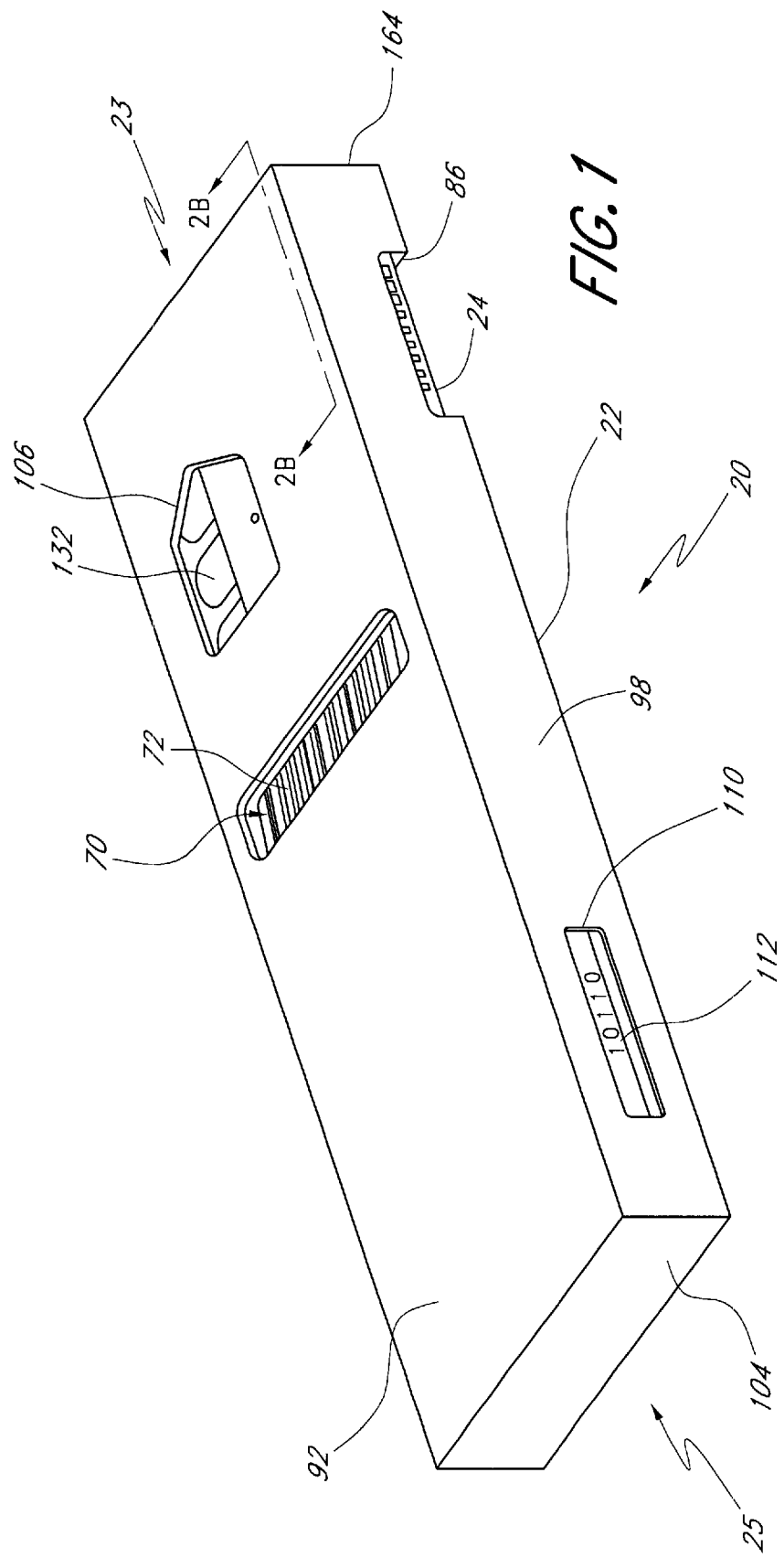
FIG. 1 is a perspective view of a cassette within a sleeve.
Figure 2:
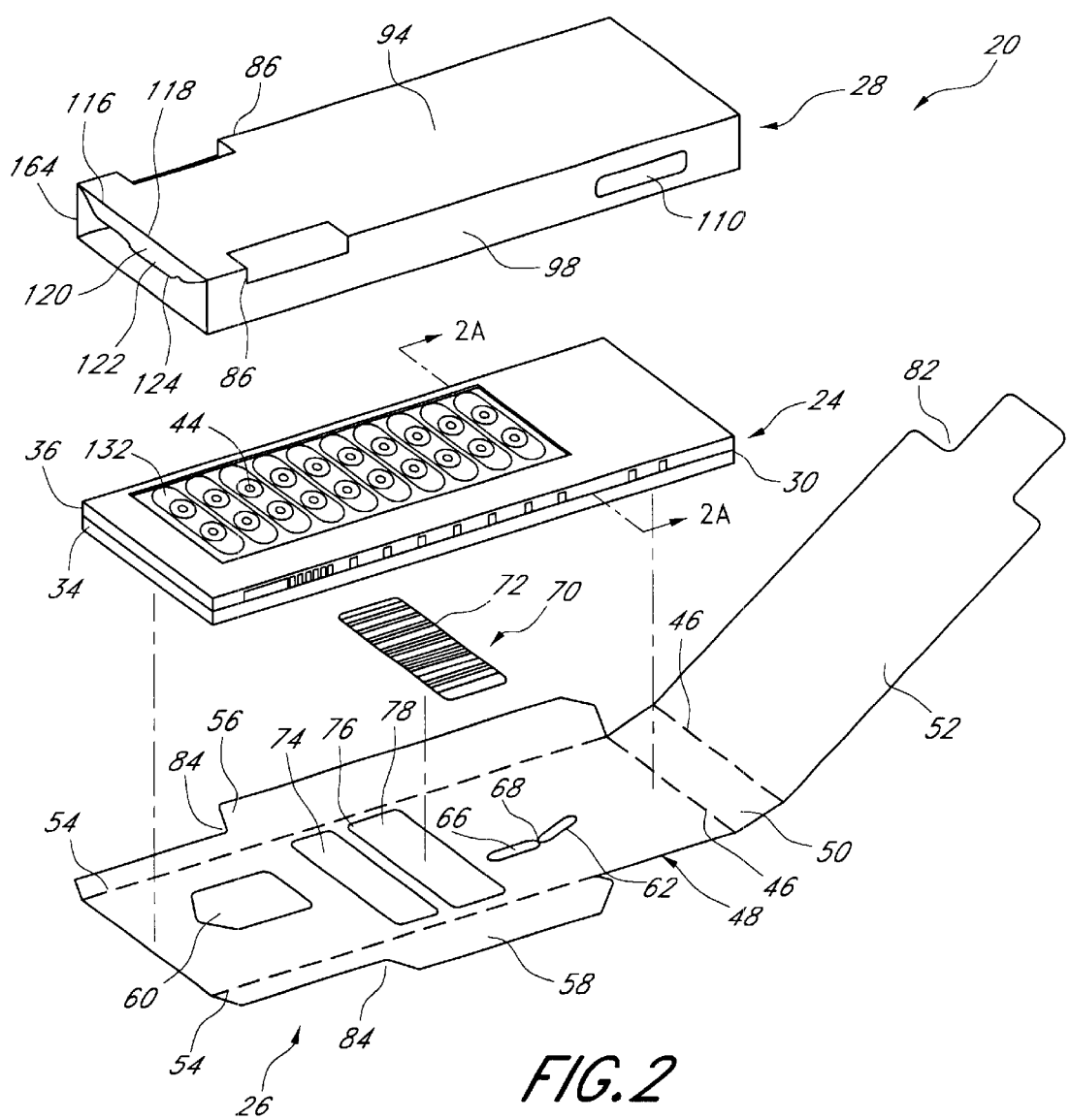
FIG. 2 is an exploded view of the cassette and sleeve of FIG. 1.
Figure 2A:
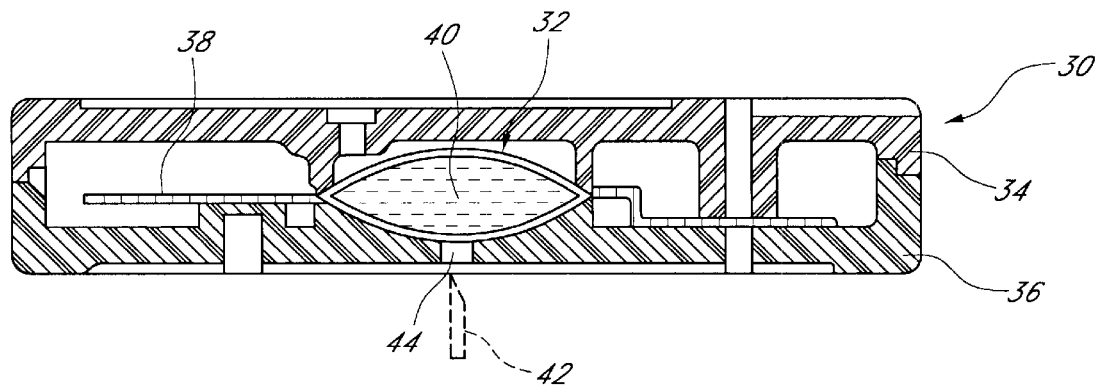
FIG. 2A is a sectional view taken along line 2A—2A of FIG. 2.

FIG. 1 illustrates an assembled cassette assembly 20 comprising a sleeve 22 containing a cassette 24. The exploded view of FIG. 2 illustrates the components of the cassette assembly 20 in more detail. The sleeve 22 has an open end 23 and a closed end 25 and comprises an inner layer 26 of corrugated cardboard and an outer layer 28 of an attractive pressboard material. The cassette 24 comprises an elongated, rectangular plastic cassette shell 30 containing a plurality of cells 32 containing a solution of 58 wt % hydrogen peroxide. As seen in FIG. 2A, the cassette shell 30 is formed of an upper housing section 34 which mates with a lower housing section 36 to capture and to enclose a cell strip 38. The cell strip 38 is formed of a flexible material and contains the cells 32. Each cell 32 contains a precisely measured amount of hydrogen peroxide 40. Of course, other liquid sterilants may be substituted therefor. Preferably, the cassette shell 30 and cell strip 38 are formed of suitable polymers, such as polystyrene and polyethylene, respectively. However, one of skill in the art will recognize that other materials may be substituted therefor.

Each of the cells 32 is accessible by a hollow needle 42 through an aperture 44 in the cassette shell 30. Returning to FIG. 2, the sleeve inner layer 26 wraps about the cassette 24. Thus, if any small droplets of the hydrogen peroxide solution are left on the outside of the cassette 24 after use, they will be absorbed by the cardboard of the sleeve inner layer 26, thereby preventing contact with an operator's hands or clothing. The sleeve inner layer 26 provides several other important functions as will become apparent. The sleeve inner layer 26 folds about a pair of parallel fold lines 46 to form an upper panel 48, an end panel 50, and a lower panel 52. A pair of longitudinal fold lines 54 forms a first side panel 56 and a second side panel 58. A large arrow shaped aperture 60 in the upper panel 48 points toward the sleeve open end 23. Also, a tab 62 comprises a small longitudinally elongate cutout that remains attached at its rearward end 66 (toward the sleeve closed end 25), thereby forming a fold line 68 about which the tab 62 rotates through 180°.

As seen in FIGS. 1 and 2, a label 70, preferably with computer readable indicia 72, such as a bar code, identifies the cassette assembly 20. A large lateral rectangular window aperture 74 in the sleeve inner layer 26 forms a window through which the label 70 becomes visible. A rectangular cutout 76 sits immediately rearward of the window aperture 74 and forms a removable panel 78 of cardboard, which fits within the cutout 76. The label 70 has adhesive on its surface opposite the indicia 72 and attaches to the removable panel 78 and to the inner sleeve upper panel 48 between the cutout 76 and window aperture 74. As shown in FIGS. 5–8, this forms a hinge 80 which allows the labels to rotate through 180° from a position as shown in FIG. 6 wherein the removable panel 78 is received within the cutout 76 and the label indicia 72 are not visible through the window aperture 74, through the position shown in FIG. 7, to the position shown in FIG. 8 wherein the label indicia 72 becomes visible through the window aperture 74.

Returning to FIG. 2, cutouts 82 at the lateral side edges of the inner sleeve lower panel 52 near the sleeve open end 23, and additional cutouts 84 aligned therewith in the inner sleeve first and second side panels 56 and 58, provide access to the cassette 24 through the sleeve inner layer 26. Similar cutouts 86 are provided in the sleeve outer layer 28 in registry with the cutouts 82 and 84 to provide access to the cassette 24 through the entire sleeve 22.

FIGS. 2 and 4 best illustrate the structure of the sleeve outer layer 28. It is formed of folded pressboard stock, but of course could be formed of other folded stock material, such as a suitable polymer, or it could be molded or formed in some other fashion to form an equivalent structure to that disclosed here. Longitudinal fold lines 90 form a top panel 92, bottom panel 94, a first side panel 96, and a second side panel 98, which correspond to the upper panel 48, lower panel 52, first side panel 56, and second side panel 58, respectively, on the sleeve inner layer 26. The longitudinal fold lines 90 also form a glue flap 100 which seals to the first side panel 96 to form the three dimensional structure of the outer sleeve layer 28. Side tabs 102 and a foldable flap 104 form the closed end 25 of the sleeve outer layer 28. Of course, other closure means such as glue flaps, may be substituted therefor. An arrow shaped aperture 106 and a rectangular window 108 in the top panel 92 register with the corresponding openings 60 and 74 in the sleeve inner layer 26. A rectangular window 110 in the second side panel 98 provides for viewing of the indicia 112 on the cassette 24.

Figure 2B:
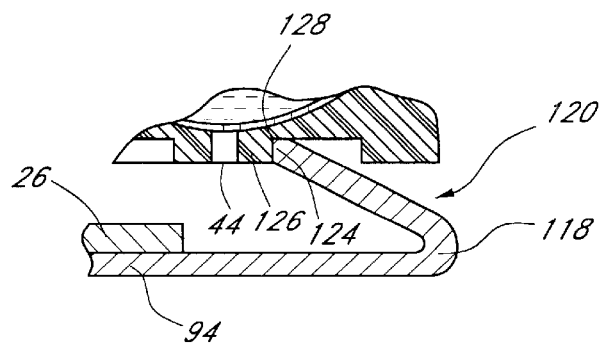
FIG. 2B is a sectional view taken along line 2B—2B of FIG. 1.
Figure 3:
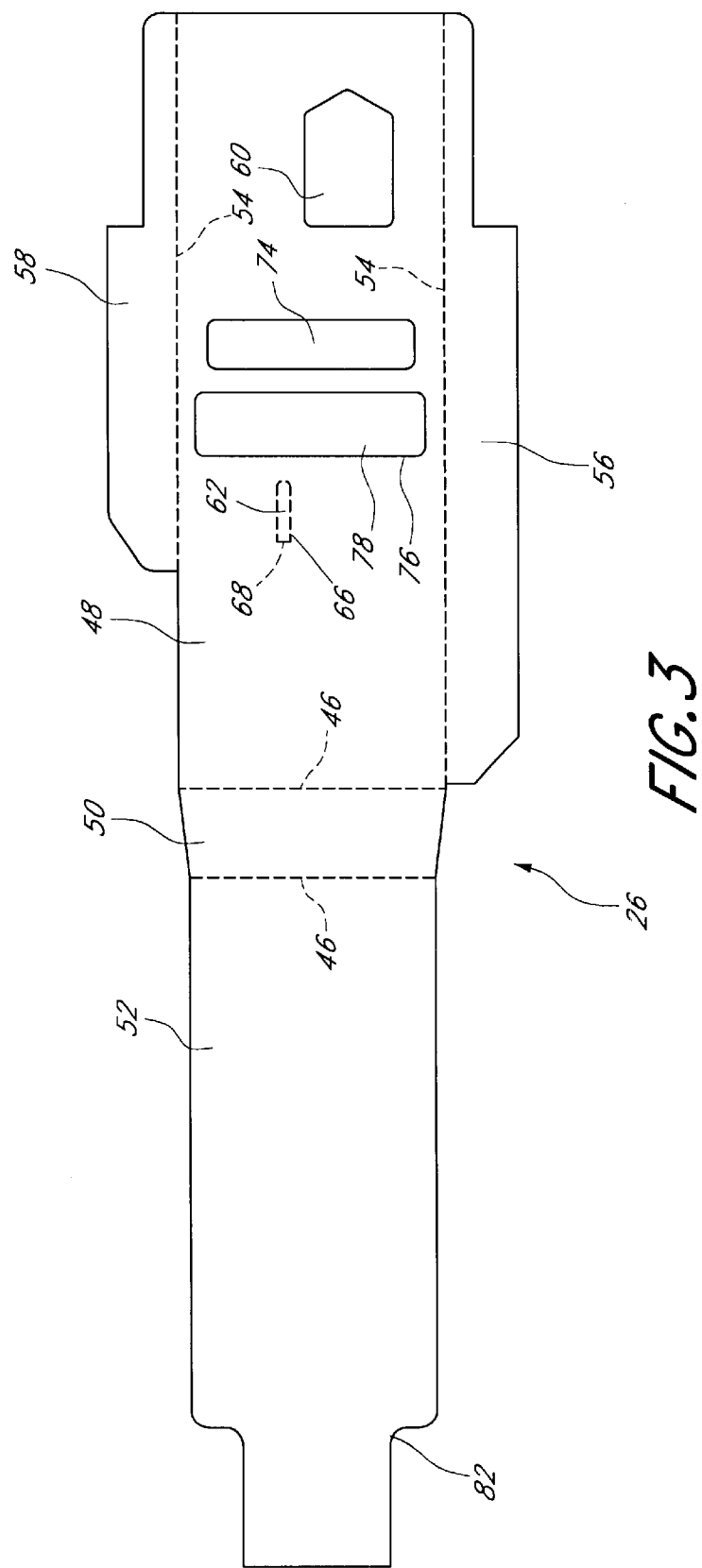
FIG. 3 is a plan view of an unfolded blank forming an inner layer of the sleeve of FIG. 1.

FIGS. 2B and 4 provide more detail on how the cassette 24 is held in place. A lateral fold line 114 at the forward end 116 of the bottom panel 94 of the sleeve outer layer 28 forms a hinge 118 about which rotates a retaining flap 120. The retaining flap 120 extends from the fold line 114 to terminate in a tang 122, a terminal edge 124 of which engages the cassette 24 to retain the cassette 24 within the sleeve 22. An annular post 126 surrounds each of the piercing apertures 44 in the cassette 24 such that the aperture 44 extends axially through the post 126. The post has a vertical annular sidewall 128 against which the terminal edge 124 abuts, as best shown in FIG. 2B. The retaining flap 120 performs a surprisingly good job of holding the cassette 24 within the sleeve 22. Even fairly vigorous shaking will not dislodge the cassette 24 from the sleeve 22.

A fresh cassette assembly 20 having its cells 32 filled with hydrogen peroxide is configured as follows: the cassette 24 is received within the sleeve inner layer 26. The label 70 is folded into the position shown in FIG. 8 wherein the label indicia 72 are visible through the window apertures 74 and 108. Also, the tab 62 is folded over 180° to face rearwardly. The cells 32 are received within chambers within the cassette shell 30, the outer surface 132 of which is rounded. The tab 62 engages this rounded outer surface 132 to provide a certain degree of resistance to movement between the cassette 24 and the sleeve 22. The sleeve inner layer 26 is received within the sleeve outer layer 28 with the retaining flap 120 folded over the sleeve inner layer 26 and into the sleeve 22 where its terminal edge 124 abuts the annular post vertical wall 128 on the cassette 24 thereby retaining the sleeve inner layer 26 and the cassette 24 within the sleeve outer layer 28.

FIG. 9 shows the cassette assembly 20 in a perspective view from the top, where the cassette 24 has been pushed through the open end 23 of the sleeve 22 to show further aspects of the cassette 24. An arrow 134 on the top of the upper housing section 34 of the cassette shell 30 indicates the forward direction of the cassette 24. Further, there are a plurality of grooves 138 extending to a right edge 140 of the cassette 24, with flat ridges 144 between the grooves 138. A flat dividing ridge 146 separates the grooves 138 from curved cell covers 150, the portion of the upper housing section 34 which cover the cells (not seen in FIG. 9). The curved cell covers 150 and underlying cells (not seen) are numbered from a forward end 154 of the cassette 24. The cell cover 150 and underlying cell closest to the forward end 154 is number one, and the cell cover 150 and underlying cell furthest from the forward end is number ten (not seen). Each of the grooves 138 has a vertical edge 156 at the portion of the groove 138 closest to the forward end 154 of the cassette 24. A slanted portion 158 of the groove 138 rises from the base of the vertical edge 156 at about a 30° angle to meet the flat ridge 144. There are ten grooves 138 on the right edge 140 of the cassette 24, corresponding to the ten cells in the cassette. Other embodiments of the cassette 24 can have different numbers of grooves 138 and cells.

Automatic Cassette Extraction Mechanism

Figure 10:
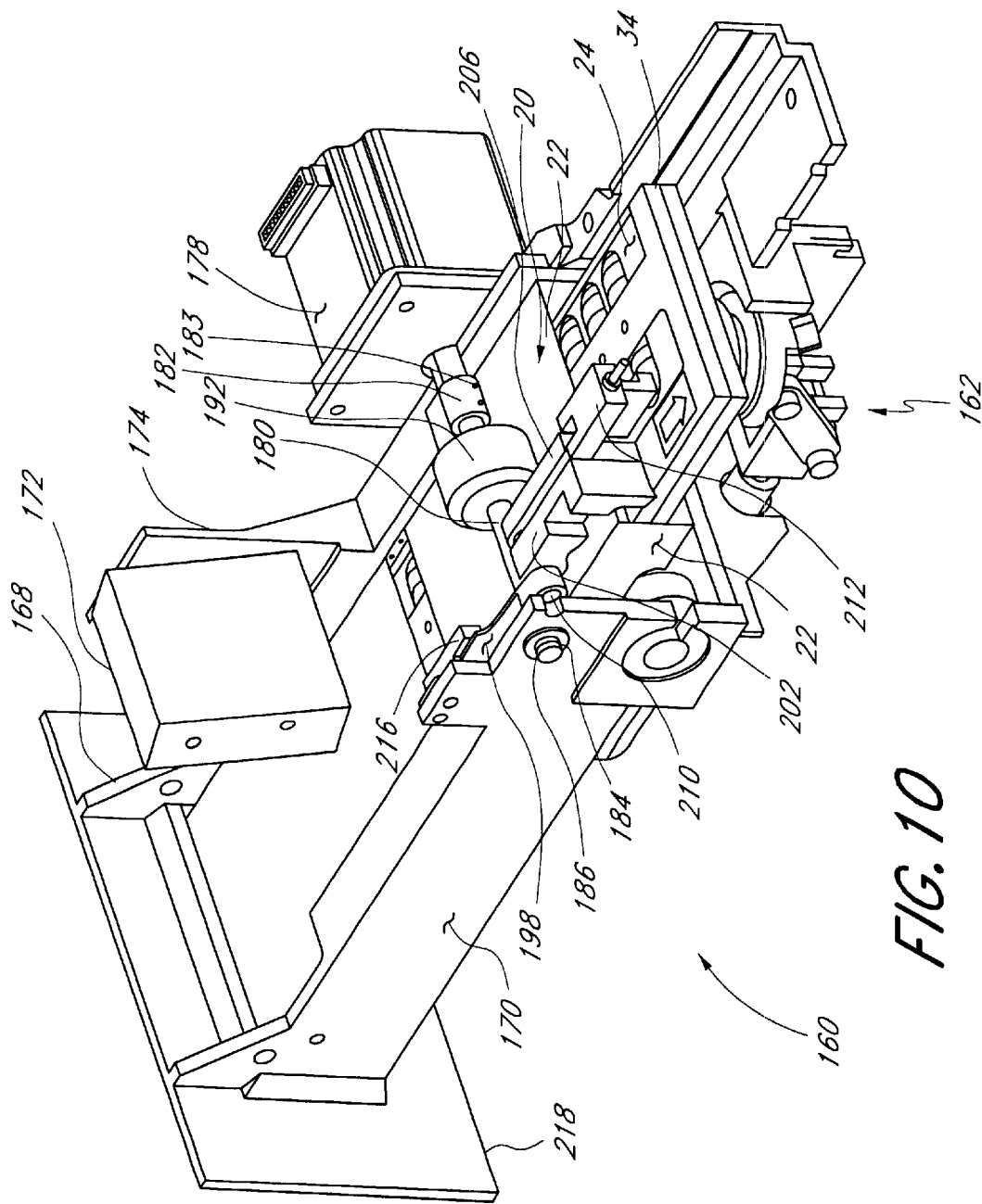
FIG. 10 is a perspective view of the cassette and sleeve of FIG. 1 positioned in a delivery system and a cassette sensing mechanism in accordance with the present invention.

The cassette assembly 20 was originally intended for use in with the cassette extraction mechanism described in U.S. Pat. No. 5,882,611. The extraction mechanism previously described has been simplified, and a cassette indexing system has been added, as described below. FIGS. 10–16 show an embodiment of an automatic cassette extraction mechanism 160. FIG. 10 shows the automatic cassette extraction mechanism 160 with the cassette assembly 20 inserted into the automatic cassette extraction mechanism 160. The cassette 24 in FIG. 10 is partially extracted from the sleeve 22 of the cassette assembly 20. An injection assembly 162 is located at the lower end of FIG. 10, under the cassette 24. The injection assembly 162 is essentially identical to the injection assembly described in U.S. Pat. Nos. 4,869,286; 4,909,287; 4,913,196; 4,938,262; and 4,941,518, herein incorporated by reference, and the injection assembly 162 will not be described in detail.

The cassette 20 is contained in the automatic cassette extraction mechanism 160 between a left machined guide 168 and a right machined guide 170. A bar code reader 172 is attached to a bar code reader bracket 174, which is part of the left machined guide 168. A motor 178 is also rigidly attached to the left machined guide 168. A shaft 180 is connected to the motor 178 through a coupler 182 at a first end, passes through a bearing 184 in the right machined guide 170, and is held in position by a shaft retaining ring 186 on a second end after passing through the right machined guide 170. The coupler 182 connects the shaft 180 to the motor 178. There are a plurality of screws 183 on the coupler 182 which can be tightened to connect the motor 178 to the shaft 180. The motor 178 may be disconnected from the shaft 180 for maintenance by simply loosening the screws 183 on the coupler 182. A top roller guide 192 is rigidly mounted on the shaft 180. The shaft 180, coupler 182, and top roller guide 192 all rotate together as the motor 178 rotates.

A first end of a flag 198, a first end of a pawl 202, and a first end of a bracket pawl 206 all pivot freely around a shoulder screw 210. The shoulder screw 210 fits into threads (not shown) on the right machined guide 170. The first ends of the flag 198, the pawl 202, and the bracket pawl 206 each comprise a round hole through which the shoulder screw 210 passes. A second end of the flag 198, pawl 202, and bracket pawl 206 may move up and down independently of one another, because the first ends of the flag 198, pawl 202, and bracket pawl 206 pivot around the shoulder screw 210. When viewed looking toward the right machined guide 170 in FIG. 10, the hole in the first end of the flag 198 is on the right side of the flag 198, and the holes in the first ends of the pawl 202 and the bracket pawl 206 are on the left ends of the pawl 202 and the bracket pawl 206, respectively. Although the first end of the pawl 202 and the first end of the bracket pawl 206 are connected to the shoulder screw 210 as a connector, other forms of connector may be used to connect to the pawl 202 and the bracket pawl 206.

Figure 15:
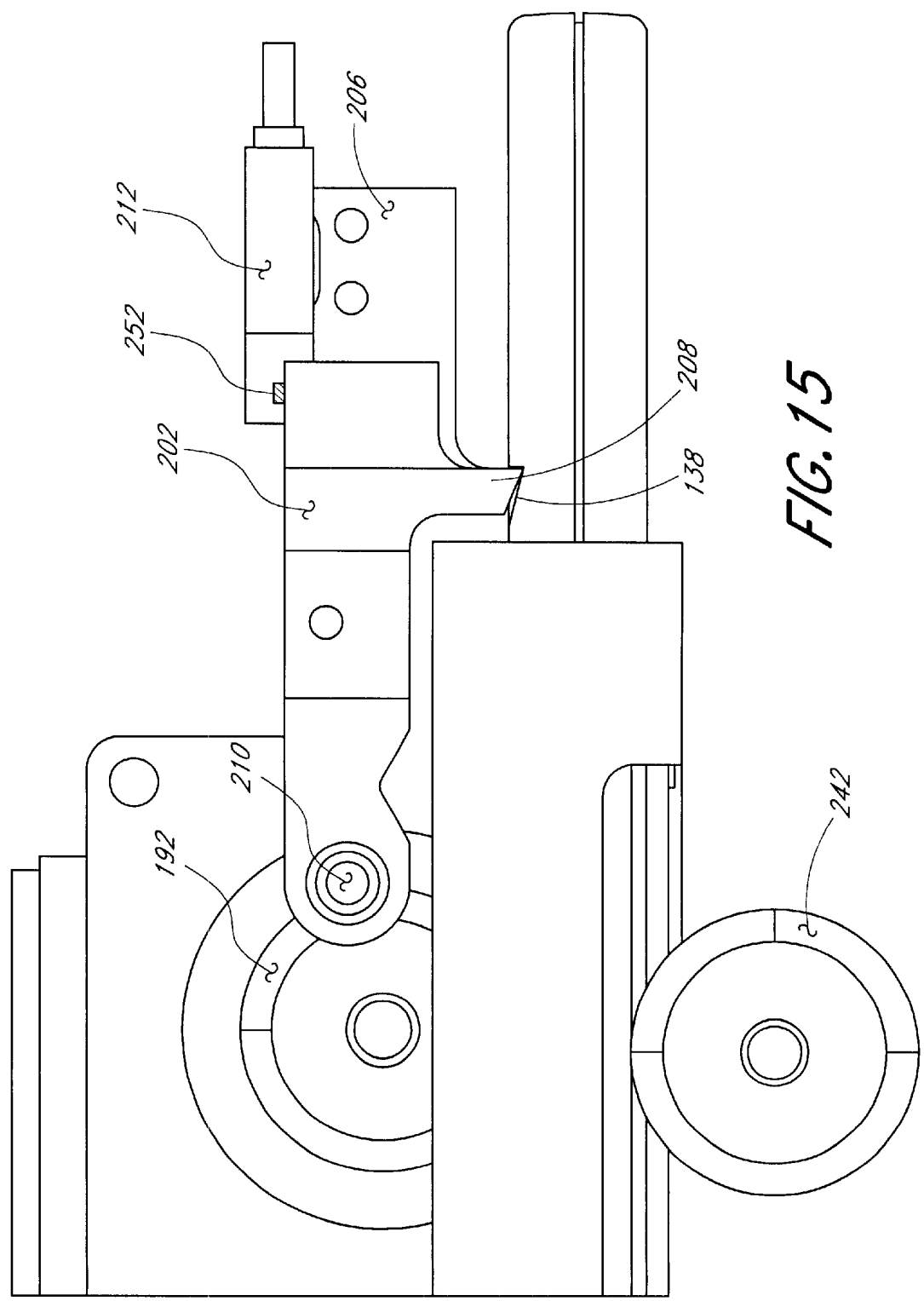
FIG. 15 is a partial cut-away side view of the cassette and sleeve of FIG. 1 positioned within the delivery system and the cassette sensing mechanism of FIG. 10 showing the position of a light beam on a sensor when the pawl on the cassette sensing mechanism is at the bottom of the groove on the cassette.
Figure 16:
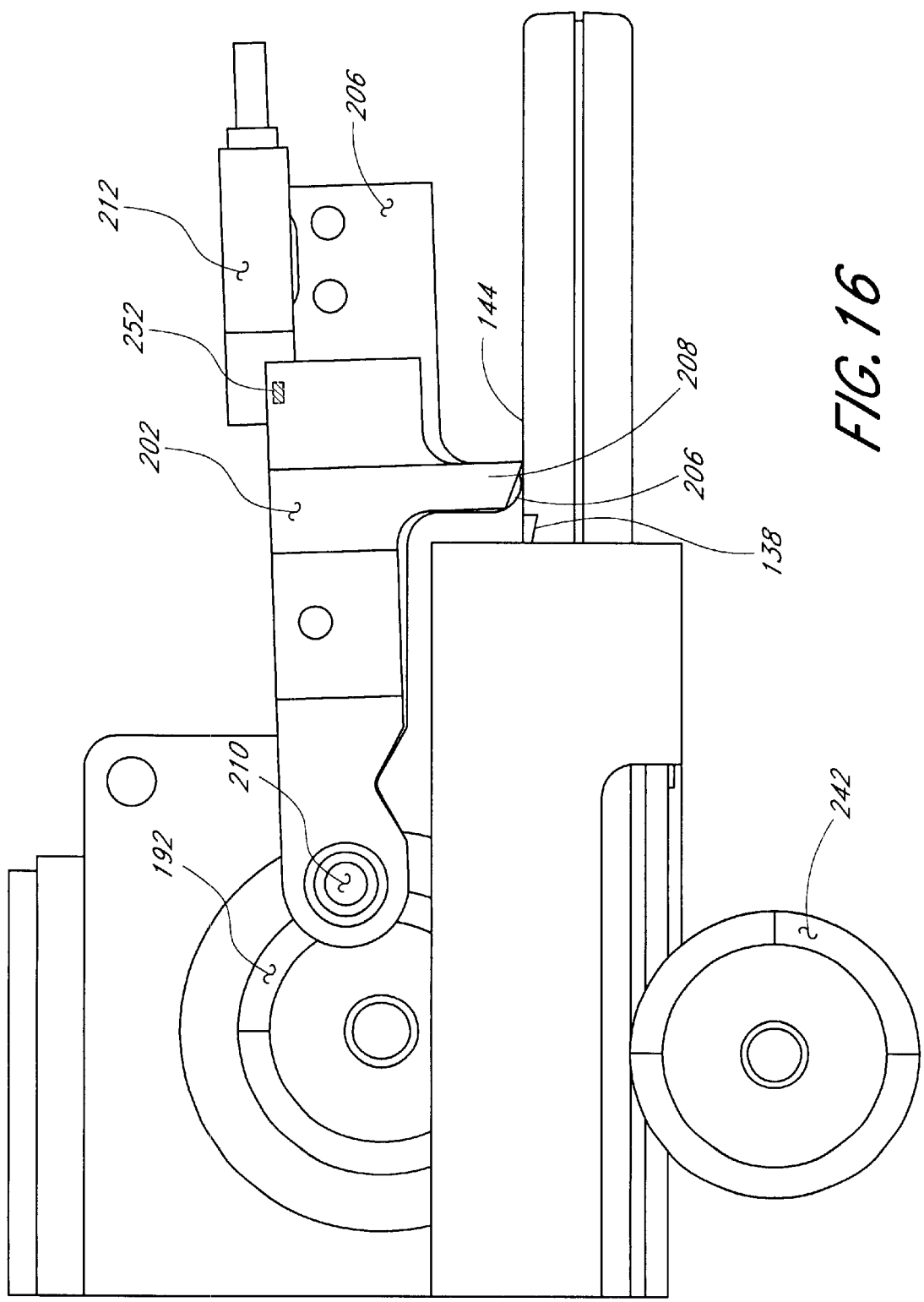
FIG. 16 is a partial cut-away side view of the cassette and sleeve of FIG. 1 positioned within the delivery system and the cassette sensing mechanism of FIG. 10 showing the position of the light beam on the sensor in phantom lines, where the pawl is on top of a flat ridge on the cassette, as when the cassette enters the delivery system.

The second end of the pawl 202 further comprises a downward-facing pawl tongue 208, best seen in FIGS. 15 and 16. When the cassette 24 is present in the automatic cassette extraction mechanism 160, and the cassette 24 has been partially extracted from the sleeve 22, the pawl tongue 208 and a lower part of the second end of the bracket pawl 206 are in contact with the upper housing section 34 of the cassette 24.

A sensor 212 is mounted on a top of the second end of the bracket pawl 206. The sensor 212 in the embodiment shown in FIG. 10 has a shape similar to a "U". The sensor 212 comprises a light source (not shown) in a first arm of the "U" and a light receptor (not shown) in a second arm of the "U". A top of the second end of the pawl 202 passes between the first and the second arms of the "U" of the sensor 212, as shown more clearly in FIGS. 14 and 17A. Although any of a number of sensors 212 are suitable for use in the apparatus and the method of the present invention, one suitable sensor 212 is the PM-R44 super small slot sensor, available from SUNX/Ramco Electric Co., 1207 Maple, West Des Moines, Iowa 50265. The sensor 212 senses the presence of the top of the pawl 202 between the two arms of the "U" of the sensor 212, because the top of the pawl 202 blocks the light from the first arm of the "U" of the sensor 212 so that the light does not reach the light receptor in the second arm of the "U" of the sensor 212. Other sensors 212 which indicate the presence of the pawl 202 may be suitable for embodiments of the apparatus and method of the present invention. The second end of the pawl 202 and the pawl tongue 208 can rise and fall independently of the motion of the bracket pawl 206 and the sensor 212 mounted on the bracket pawl 206, because the first ends of the pawl 202 and the bracket pawl both pivot freely around the shoulder screw 210.

A sleeve sensor 216 is mounted on the right machined guide 170 above the flag 198. When the cassette assembly 20 is present in the automatic cassette extraction mechanism 160, the second end of the flag 198 is pushed up by the sleeve 22 on the cassette assembly 20, causing the second end of the flag 198 to contact the sleeve sensor 216. The sleeve sensor 216 therefore senses the presence of the cassette assembly 20 in the automatic cassette extraction mechanism 160. A guide base 218 connects the left machined guide 168 and the right machined guide 170 at an end of the automatic cassette extraction mechanism 160 into which the cassette assembly 20 is inserted.

Figure 11:
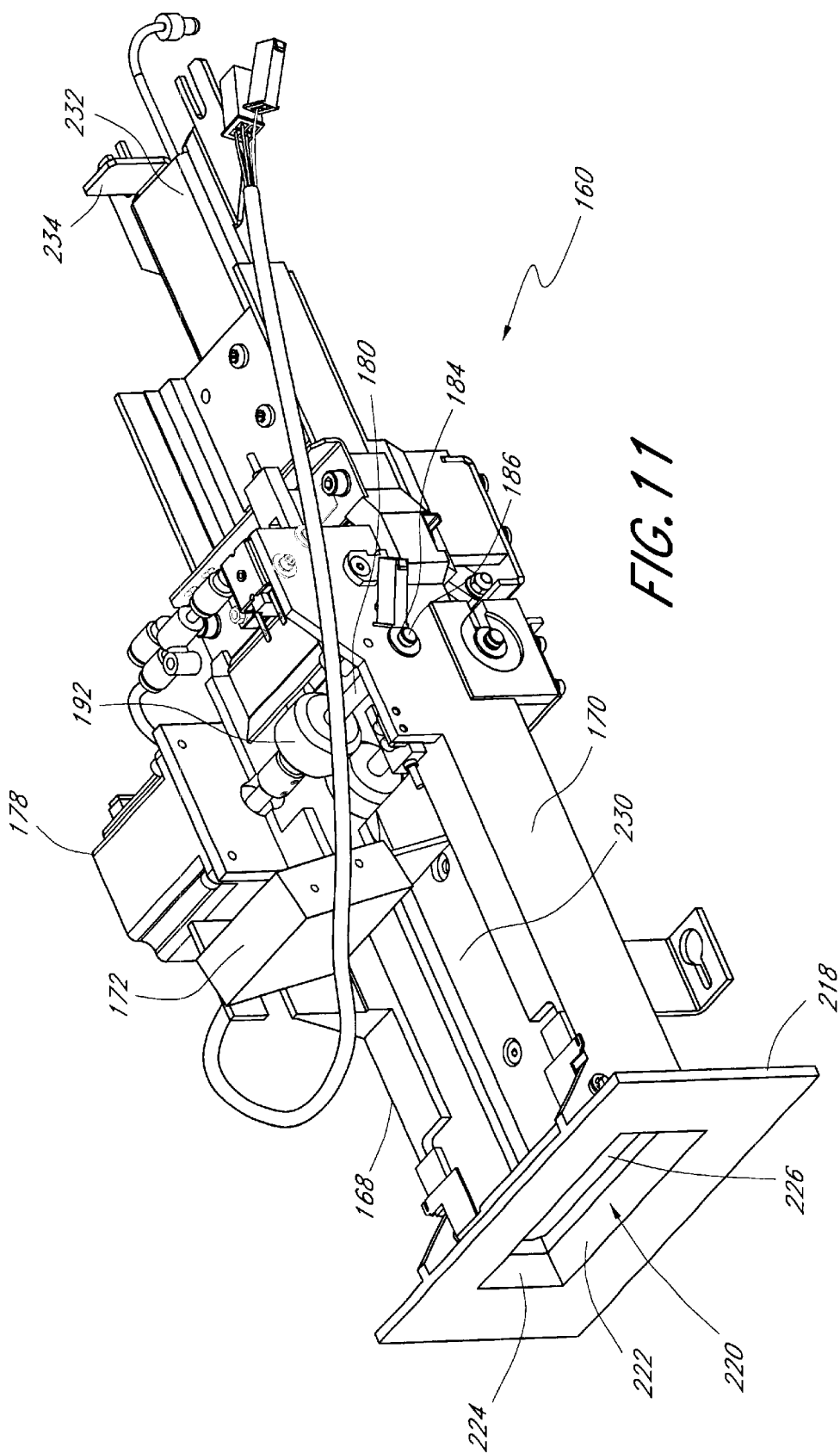
FIG. 11 is another perspective view of the delivery system and the cassette sensing mechanism of FIG. 10.

FIG. 11 is another perspective view of the automatic cassette extraction mechanism 160, showing additional aspects. No cassette assembly 20 is present in the automatic cassette extraction mechanism 160 shown in FIG. 11. The guide base 218 connecting the left machined guide 168 to the right machined guide 170 comprises a receiving slot 220 sized to receive the cassette assembly 20 with its sleeve open end 23 forward. The rectangular shaped receiving slot 220 is outlined by a lower wall 222, two side walls 224, and a top wall (not seen in FIG. 11). The receiving slot 220 is covered by a spring loaded door 226. The spring loaded door 226 closes the receiving slot 220 when no cassette assembly 20 is present in the receiving slot 220 and provides a downward biasing force against the cassette assembly 20 to hold it firmly against the lower wall 222.

The lower wall 222, two side walls 224, and the top wall lead into a rectangular shaped area outlined by the inside wall of the left machined guide 168, the inside wall of the right machine guide 170, and the top of a base plate 230 which connects the left machined guide 168 to the right machined guide 170. When a cassette assembly 20 is present in the automatic cassette extraction mechanism 160, the base plate 230 supports the cassette assembly 20. An end stop bracket 232 is attached to the base plate 230 with two screws and nuts at an end of the base plate 230 furthest away from the guide base 218. The end of the end stop bracket 232 turns upward to form an end stop 234 for the cassette 24, preventing the cassette 24 from being completely removed from the sleeve 22.

Figure 12:
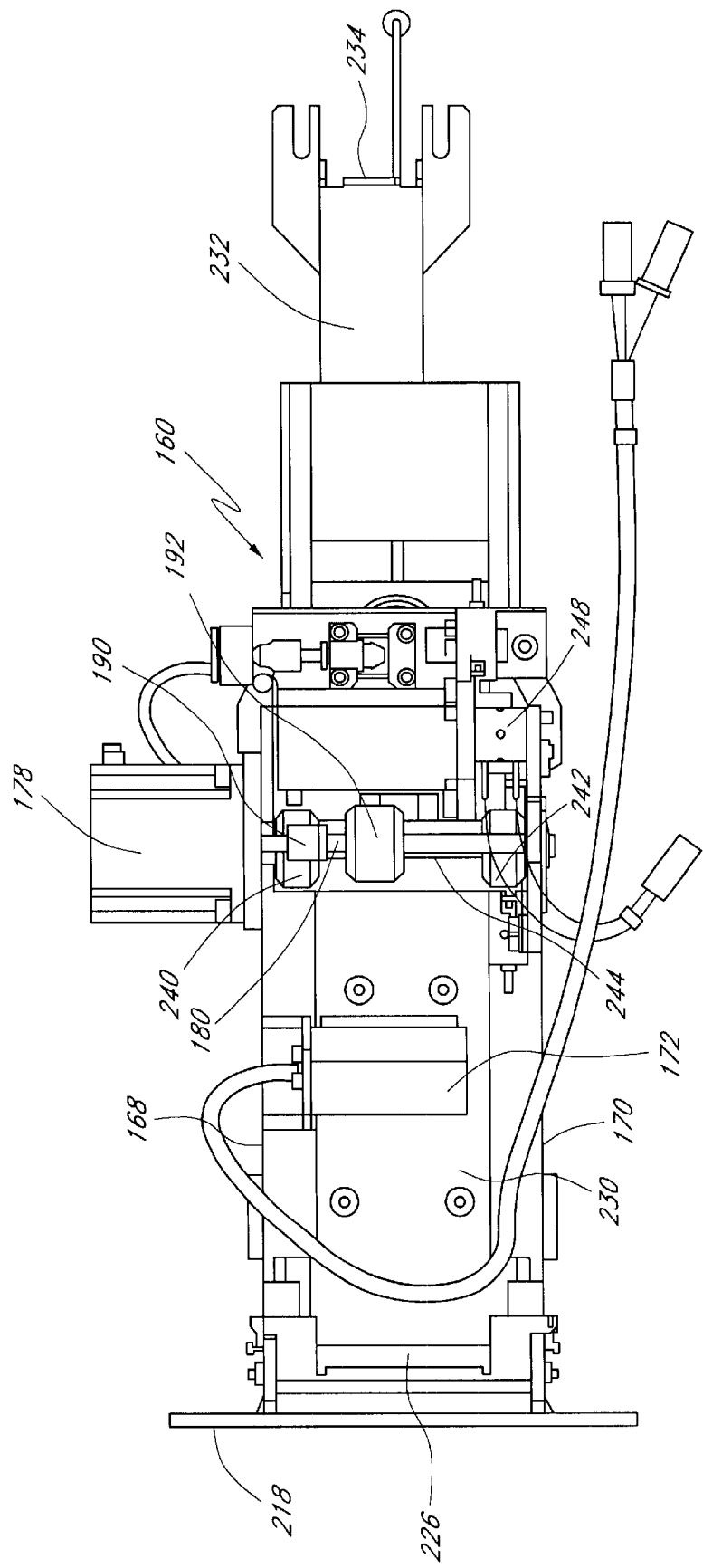
FIG. 12 is a top view of the delivery system and the cassette sensing mechanism of FIG. 10.

FIG. 12 shows the automatic cassette extraction mechanism 160 from the top. A left bottom roller guide 240 and a right bottom roller guide 242 are mounted firmly on a lower shaft 244. The lower shaft 244 extends through both the left machined guide 168 and the right machined guide 170 and is mounted on bearings so that the lower shaft 244 may rotate freely. The lower shaft 244 is not connected to the motor 178, and the lower shaft 244, the left bottom roller guide 240, and the right bottom roller guide 242 rotate freely and independently of the shaft 180 and the top roller guide 192 when there is no cassette assembly 20 in the automatic cassette extraction mechanism 160. A solenoid 248 is mounted on the right machined guide 170. When the solenoid 248 is activated, the solenoid 248 lifts the pawl 202.

Figure 13:
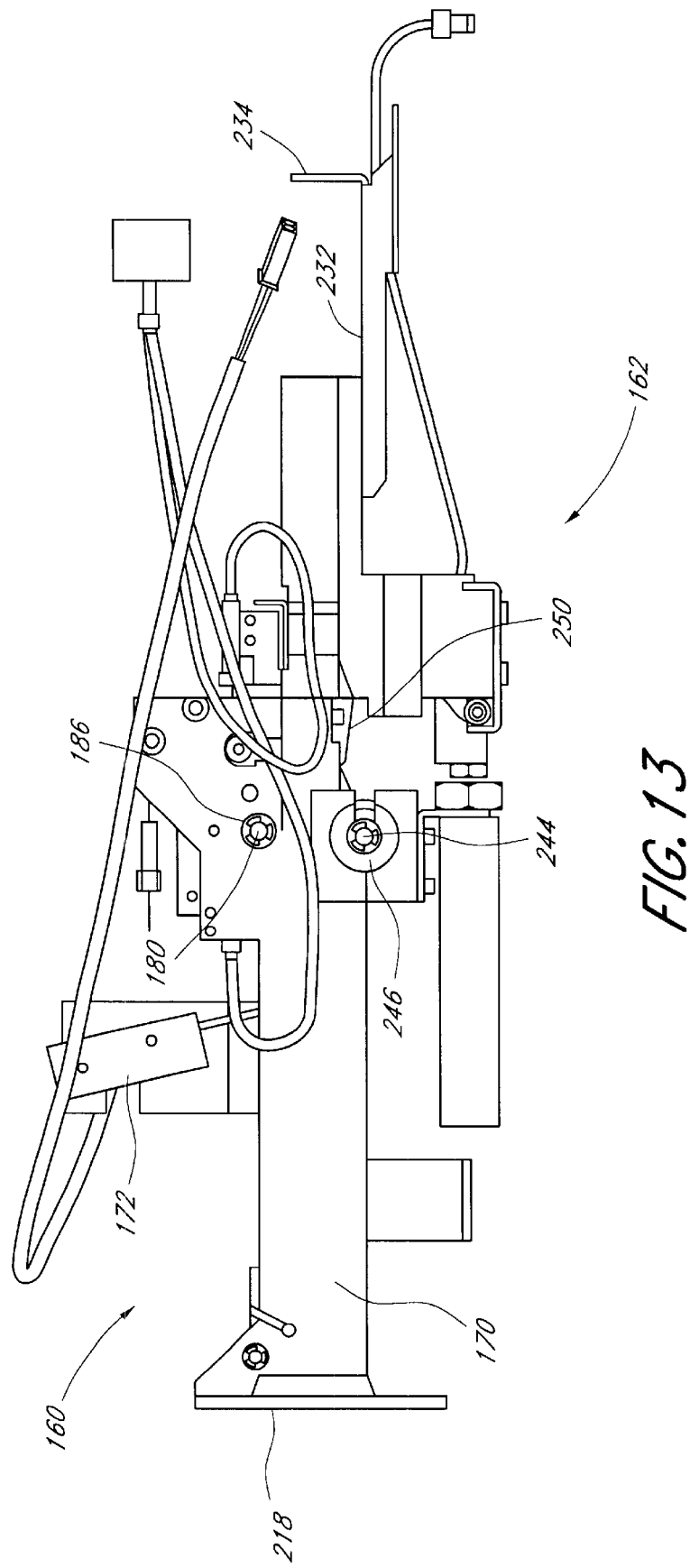
FIG. 13 is a side view of the delivery system and the cassette sensing mechanism of FIG. 10.

FIG. 13 shows a side view of the automatic cassette extraction mechanism 160 and the injection system 162. The relative positions of the shaft 180 and the lower shaft 244 are seen in FIG. 13. The lower shaft 244 is retained in place by a lower shaft retaining ring 246 on each end of the lower shaft 244. A flap opener 250 is mounted on a bottom of the right machined guide 170.

Operation of the Automatic Cassette Extraction Mechanism

The operation of the automatic cassette extraction mechanism 160 with the cassette sensing mechanism is described next.

Insertion of the Cassette Assembly into the Automatic Cassette Extraction Mechanism The cassette assembly 20 with its sleeve open end 23 forward is inserted into the receiving slot 220 of the automatic cassette extraction mechanism 160. Inserting the cassette assembly 20 into the automatic cassette extraction mechanism 160 lifts the second end of the flag 198. The second end of the flag 198 contacts the sleeve sensor 216, sending a signal to the control unit (not shown), such as the control unit used for the sterilization process. Any suitable control unit may be employed, such as a microprocessor-based automatic control system, and multiple controllers may be used for controlling various aspects of the operation described herein. The control unit activates the bar code reader 172. The bar code reader 172 reads the label indicia 72 on the cassette 24 through the lateral rectangular aperture 74 on the inner layer 26 and the rectangular window 108 on the outer layer 28 of the sleeve 22. The label information, including the lot code and shelf life data, is fed into the control unit. If the cassette 24 has exceeded the allowed shelf life or is otherwise defective, the cassette 24 is rejected, and the cassette assembly 20 is removed from the automatic cassette extraction mechanism 160.

If the cassette is acceptable for use, the control unit activates the motor 178, and the motor turns counterclockwise, rotating the top roller guide 192. The rotating top roller guide 192 contacts the top panel 92 of the outer layer 28 of the sleeve 22, pulling the cassette assembly 20 further into the automatic cassette extraction mechanism 160. The left bottom roller guide 240 and the right bottom roller guide 242 contact the bottom panel 94 of the outer layer 28 of the sleeve 22 and are rotated by the movement of the cassette assembly 20.

When the cassette assembly 20 has moved a sufficient distance into the automatic cassette extraction mechanism 160, a forward edge 164 of the sleeve 22 contacts the flap opener 250 (seen in FIG. 13), stopping the movement of the sleeve 22. The flap opener 250 slides between the cassette 24 and the retaining flap 120 to rotate the retaining flap 120 downward and out of engagement with the cassette 24. When the forward edge 164 of the sleeve 22 is in contact with the flap opener 250, the cassette assembly 20 has moved a sufficient distance into the automatic cassette extraction mechanism 160 so that the top roller guide 192 contacts the top of the cassette 24 through the arrow shaped aperture 60 in the inner layer 26 and the arrow shaped aperture 106 in the outer layer 28 of the sleeve 20. The flap opener 250 stops the motion of the sleeve 22 so that the rotation of the top roller guide 192 pulls the cassette 24 through the open end 23 of the outer layer 28 of the sleeve 20, as shown in FIG. 10.

The left bottom roller guide 240 and the right bottom roller guide 242 contact the cassette 24 through the cutouts 82 and 84 in the inner layer 26 and cutouts 86 in the outer layer 28 of the sleeve 22. The cutouts 82, 84, and 86 are shown in FIG. 2. The left bottom roller guide 240 and the right bottom roller guide 242 are free-wheeling and rotate when the cassette 24 is moved by the rotation of the top roller guide 192. The left bottom roller guide 240 and the right bottom roller guide 242 simply support the cassette and do not help to pull the cassette 24 out of the sleeve 20.

Relative Motions of the Pawl and the Bracket Pawl

Figure 14:
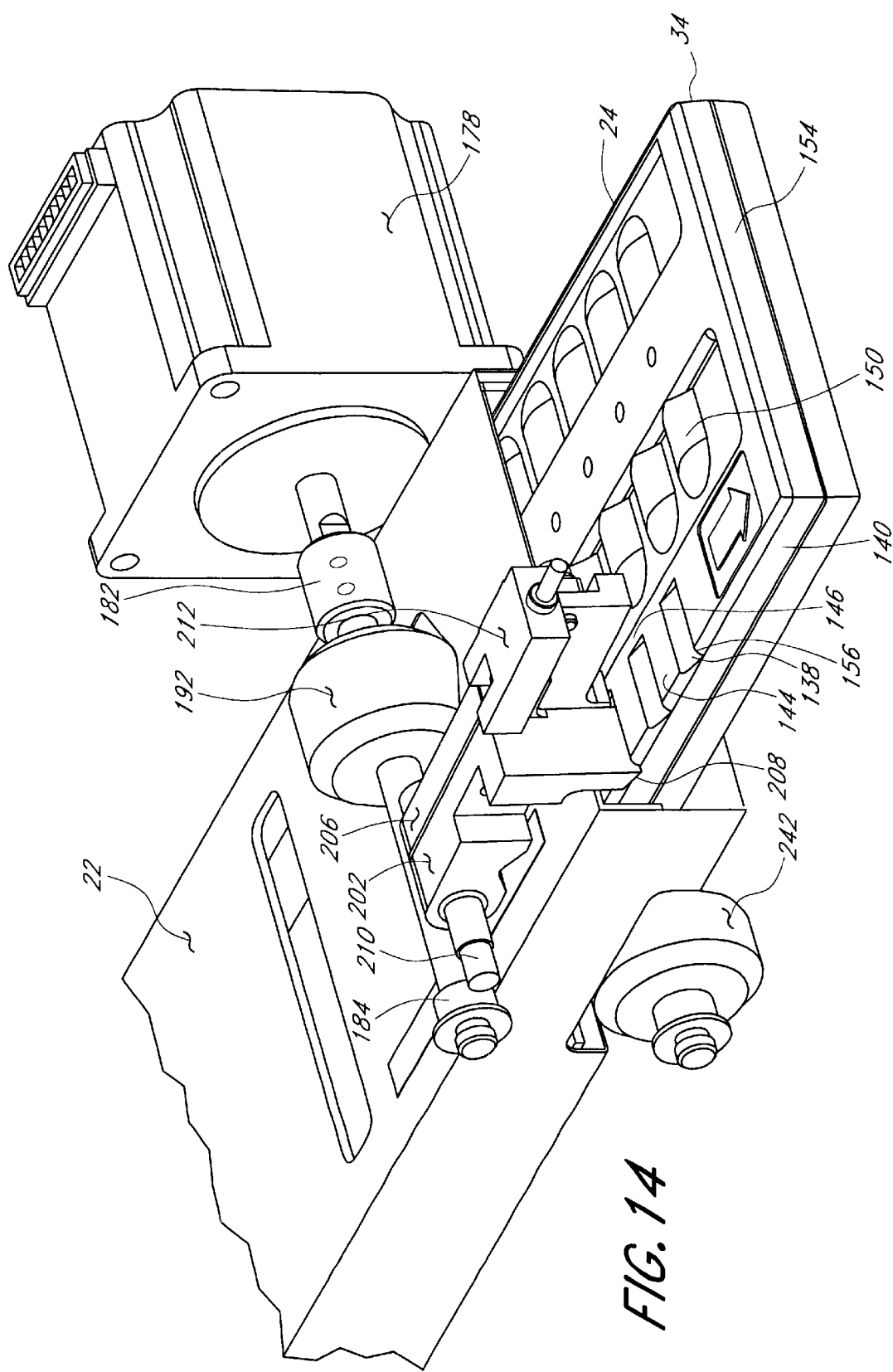
FIG. 14 is a partial cut-away perspective view of the cassette and sleeve of FIG. 1 positioned within the delivery system and the cassette sensing mechanism of FIG. 10 showing a pawl in the cassette sensing mechanism resting in a groove on the cassette.

FIG. 14 shows the cassette 24 in the automatic cassette extraction mechanism 160 after the cassette 24 has been partially extracted from the sleeve 22. Several components of the automatic cassette extraction mechanism 160, including the solenoid 248, have been omitted from FIG. 14 for clarity. The top of the second end of the pawl 202 is located between the two arms of the "U" of the sensor 212 on top of the bracket pawl 206, as is shown more clearly in FIG. 17A. The pawl tongue 208 and the bottom of the second end of the bracket pawl 206 rest on the upper housing section 34 of the cassette shell 30.

The operation of the cassette sensing mechanism portion of the automatic cassette extraction mechanism 160 depends on the relative motions of the pawl 202 and the bracket pawl 206 as the cassette 24 passes through the automatic cassette extraction mechanism 160. The motions of the pawl 202 and the bracket pawl 206 are therefore described before describing the remaining operations of the automatic cassette extraction mechanism 160.

FIG. 14 shows that the pawl tongue 208 and the bottom of the second end of the bracket pawl 206 rest on different portions of the upper housing 34 of the cassette shell 30. In FIG. 14, the pawl tongue 208 is resting at the bottom of the third groove 138 extending to the right edge 140 of the cassette 24. The bottom of the second end of the bracket pawl 206 is resting on the flat dividing ridge 146 separating the grooves 138 from the curved cell covers 150.

As the cassette 24 moves through the automatic cassette extraction mechanism 160 with the rotation of the top roller guide 192, the pawl tongue 208 and the second end of the pawl 202 rise and fall as the pawl tongue 208 traverses the groove 138, the slanted portion 158 of the groove 138, and the flat ridge 144 on the upper housing section 34 of the plastic cassette shell 30.

For example, if the pawl tongue 208 in FIG. 14 were in the bottom of the first groove 138, the pawl tongue 208 would rise as the pawl tongue 208 traverses the slanted portion 158 of the groove until the pawl tongue 208 encounters the flat ridge 144. The vertical position of the pawl tongue 208 remains constant as the pawl tongue 208 traverses the flat ridge 144. The pawl tongue 208 then falls into the second groove 138. The pawl tongue 208 and the second end of the pawl 202 therefore rise and fall as the pawl tongue 208 traverses the grooves 138, the slanted portions 158 of the grooves 138, and the flat ridges 144 on the surface of the upper housing section 34 of the cassette shell 30.

By contrast, the bottom of the second end of the bracket pawl 206 rests on the flat dividing ridge 146, which separates the grooves 138 from the curved cell covers 150. As the cassette 24 moves through the automatic cassette extraction mechanism 160, the second end of the bracket pawl 206 remains at the same vertical level, because the height of the flat dividing ridge 146 is constant. The pawl tongue 208 and the second end of the pawl 202 rise and fall as the cassette 24 travels through the automatic cassette extraction mechanism 160, while the second end of the bracket pawl 206 remains at the same vertical level throughout.

Determination of the Position of the Pawl on the Cassette with the Sensor

FIGS. 15 and 16 illustrate how the relative vertical positions of the pawl 202 and the bracket pawl 206 can be used to determine the position of the pawl tongue 208 on the upper housing section 34 of the cassette shell 30.

In FIG. 15, the pawl tongue 208 is in the bottom of the groove 138. The second end of the pawl 202 is therefore in as low a vertical position as possible for a situation in which the pawl tongue 208 is in contact with the upper housing section 34 of the cassette shell 30. The vertical position of the second end of the bracket pawl 206 is fixed when the second end of the bracket pawl 206 is in contact with the upper housing section 34 of the cassette shell, because the second end of the bracket pawl 206 is in contact with the flat dividing ridge 146 on the cassette shell 30. The flat dividing ridge 146 does not vary in height.

An arm on the "U" of the sensor 212 closer to the right machined guide 170 is not shown for purposes of clarity in FIG. 15 in order to clearly show the position of the top of the second end of the pawl 202. The top of the second end of the pawl 202 is located between the two arms of the "U" on the sensor 212, as is shown more clearly in FIG. 17A, and the top of the second end of the pawl 202 would not be seen clearly if the arm of the "U" of the sensor 212 closest to the right machined guide 170 were not omitted. A light beam 252 on the remaining arm of the "U" of the sensor 212 on the bracket pawl 206 is seen above the top of the second end of the pawl 202. The light receptor (not seen) on the omitted arm of the "U" on the sensor 212 would therefore receive the light beam 252 when the pawl tongue 208 is in the bottom of the groove 138, as it is shown in FIG. 15.

In FIG. 16, the pawl tongue 208 is in contact with the flat ridge 144 on the upper housing section 34 of the cassette 24 between a first groove 138 and the arrow 134 on the cassette shell 30, as seen in FIG. 9. The flat ridge 144 between the first groove 138 and the arrow 134 has the same height as the remaining flat ridges 144 on the cassette shell 30. In FIG. 16, the arm on the "U" of the sensor 212 closest to the right machined guide 170 has not been removed, as in FIG. 15.

The flat ridge 144 on the upper housing section 34 of the cassette 24 is higher than the groove 138. As shown in FIG. 16, the vertical position of the top of the second end of the pawl 202 is high enough when the pawl tongue 208 is in contact with the flat ridge 144 that the second end of the pawl 202 blocks the light beam 252 (shown in phantom lines in FIG. 16). The light receptor (not shown) on the second arm of the "U" of the sensor 212 is therefore not exposed to the light beam 252 when the pawl tongue 208 is on the flat ridge 144 on the upper housing section 34 of the cassette.

If the pawl tongue 208 is in the bottom of the groove 138, as in FIG. 15, the light receptor on the sensor 212 observes the light beam 252. If the pawl tongue 208 is in contact with the flat ridge 144, the top of the pawl 202 blocks the light beam 252, because the top of the pawl 202 is in a higher vertical position than when the pawl tongue 208 is in the groove 138. It can therefore be determined whether the pawl tongue 208 is in the groove 138 or on the flat ridge 144 by determining whether the pawl 202 blocks the light beam 252 on the sensor 212. If the light beam 252 is blocked, the light beam 252 will not be received by the light receptor on the second arm of the "U"-shaped sensor 212.

Description of the Operation of the Automatic Cassette Extraction Mechanism

Returning to the operation of the automatic cassette extraction mechanism 160, when the user inserts the cassette assembly 20 into the automatic cassette extraction mechanism 160, the flag 198 is lifted by the cassette assembly 20 and contacts the sleeve sensor 216. The sleeve sensor 216 sends a signal to the central processor (not shown), activating the motor 178 to turn counterclockwise. The top roller guide 192 pulls the cassette 24 out of the sleeve 22. The forward edge 164 of the sleeve 20 lifts both the pawl 202 and the bracket pawl 206. The pawl 202 blocks the light beam 252 on the sensor 212 on the bracket pawl 206 (see FIG. 16).

The software in the central processor turns on a clock to measure the time that the pawl 202 and the bracket pawl 206 ride together before the pawl 202 reaches the groove 138. When the pawl 202 reaches the groove 138, the pawl tongue 208 drops into the groove 138, opening the light beam 250 (see FIG. 15). The software reverses the motor 178 to rotate clockwise so that the pawl tongue 208 contacts the vertical edge 156 of the groove 138.

At this point, the cell 32 is properly located for injection. The needle 42 on the injection assembly 162 penetrates the cell 32 (see FIG. 2A) in the cassette 24. The hydrogen peroxide 40 or other sterilant in the cell 32 is drawn out and is delivered to a sterilization chamber. Operation of this mechanism is more fully described in the Williams et al. U.S. Pat. No. 4,817,800 issued Apr. 4, 1989; U.S. Pat. No. 4,913,196 issued Apr. 3, 1990; U.S. Pat. No. 4,938,262 issued Jul. 3, 1990; and U.S. Pat. No. 4,941,518 issued Jul. 17, 1990, all of which are incorporated by reference.

When the next cell 32 is to be utilized, the software turns on the motor 178 to rotate the motor 178 counterclockwise. The clock is also turned on when the motor 178 is activated.

As the pawl tongue 208 traverses the slanted portion 158 of the groove 138, the pawl tongue 208 and the second end of the pawl 202 are lifted by the contact with the slanted portion 158 of the groove. At some point, the top of the second end of the pawl 202 blocks the light beam 252. The light beam 252 remains blocked by the top end of the pawl 202 as the pawl tongue 208 traverses the flat ridge 144. When the pawl tongue 208 drops into the next groove 138, the light beam 252 is no longer blocked by the top of the pawl 202, and the signal from the sensor 212 is sent to the control unit. The software in the control unit reverses the motor 178 to rotate clockwise, so that the pawl tongue 208 contacts the vertical edge 156 of the groove 138. The needle 42 on the injection assembly 162 penetrates the cell 32 (see FIG. 2A) in the cassette 24 again. The hydrogen peroxide 40 or other sterilant in the cell 32 is drawn out and is delivered to a sterilization chamber. The process is repeated until the last cell 32 has been used. The central processor records the number of cells that have been processed and therefore determines when all of the cells have been used and the cassette 24 is spent.

At this point, the software activates the solenoid 248 and turns on the motor 178 to rotate the motor 178 clockwise. When the solenoid 248 is activated, the pawl 202 is lifted, lifting the pawl tongue 208 out of the groove 138 on the cassette 24. The rotation of the motor 178 rotates the top roller guide 192, pushing the spent cassette 24 into the sleeve 22. By lifting the pawl 202 by activating the solenoid 248, the pawl tongue 208 is not stopped by the vertical edge 156 of the groove 138 on the cassette 24. As the cassette 24 moves into the sleeve 22, the rearward end of the cassette 24 contacts the label 70, causing it to rotate backwards to the position illustrated in FIG. 6, wherein the label indicia 72 are not visible exterior of the sleeve 22. After the cassette 24 has been pushed back into the sleeve 22, the top roller guide 192 contacts the top panel 92 of the outer layer 28 of the sleeve, pushing the cassette assembly 20 out of the receiving slot 220.

Because both the pawl 202 and the bracket pawl 206 pivot around the same shoulder screw 210, the cassette sensing mechanism is more forgiving of variations in thickness of the device to be measured than previous devices. Because the pawl 202 and the bracket pawl 206 travel side-by-side on different paths on the surface of the device to be measured, the cassette sensing mechanism is sensitive to the difference in height between the surface which the pawl tongue 208 of the pawl 202 traverses and the surface which the bottom of the second end of the bracket pawl 206 traverses. Variations in thickness or undulations on the surface of the measured device do not matter significantly, because the cassette sensing mechanism is sensing the difference in height between two surfaces which are relatively close to one another, rather than measuring an absolute thickness, which can vary far more than the relative thickness of two portions of the surface of the object in close proximity to one another.

Further, unlike other previous devices, the sensitivity of the apparatus and method of the present invention does not vary with the thickness of the device being measured. The apparatus and the method measure variations in the thickness of the device on an absolute basis rather than on a percentage basis. Thus, the pawl tongue 208 and the bracket pawl 206 traverse two paths on the surface. The sensor 212 determines whether the top end of the pawl 202 is blocking the light beam 252 in the sensor 212. Whether the top end of the pawl 202 is blocking the light beam depends on the difference in height between the path on which the pawl tongue 208 rests and the path on which the bracket pawl 206 rests. The sensitivity of the sensor 212 does not depend on the thickness of the device being measured.

Other embodiments of sensors 212 can be utilized in embodiments of the apparatus and the method of the present invention. Some embodiments of sensors 212 which can be used in embodiments of the apparatus include electromechanical switches and proximity sensors. Suitable mechanical switches for use in embodiments of the apparatus are microswitches available from Honeywell Inc., 11 West Spring Street, Freeport, Ill. 61032. In particular, the MICRO SWITCH™ V7 series of microswitches are suitable for use in the apparatus, though a wide variety of electromechanical switches are suitable for use in embodiments of the apparatus of the present invention.

Suitable proximity sensors for use in embodiments of the apparatus of the present invention are available from OMRON ELECTRONICS, INC., One East Commerce Drive, Schaumburg, Ill. 60173. Two types of proximity sensors which are suitable for use in the apparatus of the present invention are inductive proximity sensors, for example, the E2E series of inductive proximity sensors, and capacitive proximity sensors, for example the E2K-X series of capacitive proximity sensors, both available from OMRON. Other forms of sensors 212 which are suitable for use with the apparatus of the present invention will be apparent to those of ordinary skill in the art.

Embodiments of the apparatus and the method of the present invention can also be used to detect unevenness or "bumps" on the surface of an object rather than simply variations in thickness. By utilizing various embodiments of the apparatus, the uneven surface to be detected can be on the top, side, or bottom of an object. The apparatus and method are therefore not limited to variations in thickness or unevenness on the top of an object.

Figure 17A:
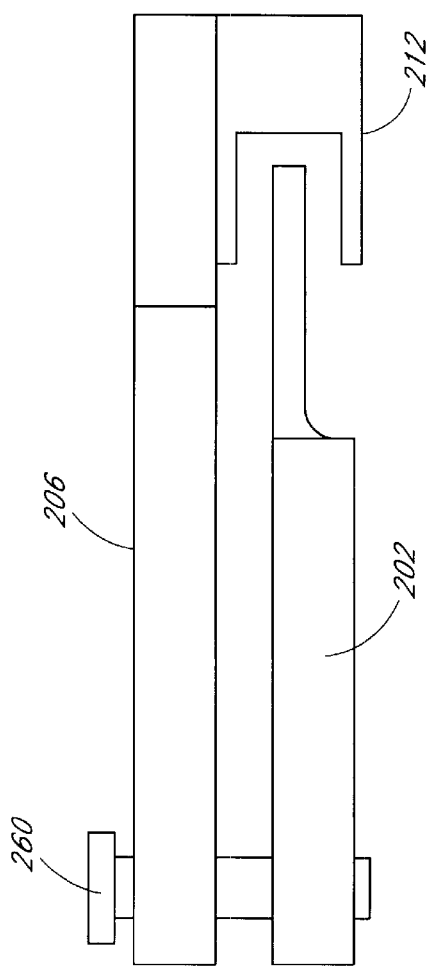
FIG. 17A is a schematic top view of a portion of an embodiment of the cassette sensing mechanism in which the pawl and the pawl bracket are mounted on a common pivot.
Figure 17B:
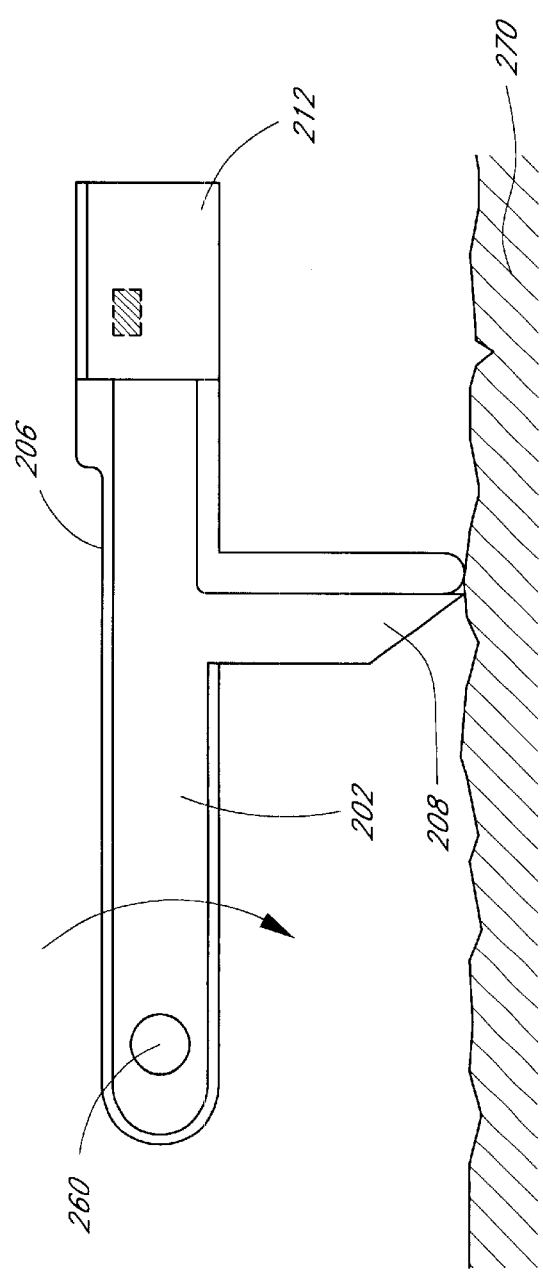
FIG. 17B is a schematic side view of the cassette sensing mechanism of FIG. 17A.

Further, the apparatus is not limited to rotational motion of the pawl 202 and the bracket pawl 206 on a single pivot point as a connector, such as the embodiment with the shoulder screw 210, as previously described and shown. For example, the pawl 202 and the bracket pawl 206 may be located on two pivot points as connectors, though the embodiment where the pawl 202 and the bracket pawl 206 are located on a single pivot point is preferred. In other embodiments, the pawl 202 and bracket pawl 206 move linearly rather than rotationally. FIGS. 17–19 show embodiments of the mounting relationships of the pawl 202, bracket pawl 206, and sensor 212 in embodiments of the apparatus of the present method. FIGS. 17A and 17B show top and side views of a portion of an apparatus in accordance with an embodiment of the present invention in which the pawl 202 and bracket pawl 206 are mounted on a single pivot 260 as a connector. The embodiment of FIGS. 17A and 17B is similar to the embodiment shown in FIG. 10. The shoulder screw 210 of FIG. 10 is an embodiment of the pivot 260 of FIGS. 17A and 17B.

The sensor 212 in FIGS. 17A and 17B is mounted on the side of the bracket pawl 206. The embodiment of the sensor 212 in FIGS. 17A and 17B is similar to the embodiment of the sensor 212 shown in FIG. 10, where the sensor 212 is "U" shaped. FIG. 17A shows clearly how the second end of the pawl 202 is laterally located between the two arms of the "U" on the sensor 212.

FIG. 17B shows a side view of the pivot 260, pawl 202, bracket pawl 206, and the sensor 212, showing how the first ends of the pawl 202 and bracket pawl 206 are both mounted on the single pivot 260 as a connector. The bottom of the bracket pawl 206 and the pawl tongue 208 on the pawl 202 are both in contact with a detecting surface 270. The first ends of the pawl 202 and the bracket pawl 206 both rotate around the single common pivot 260, allowing the bottom of the bracket pawl 206 and the pawl tongue 208 to independently rise and fall as the bottom of the bracket pawl 206 and the pawl tongue 208 contact bumps or unevenness on the detecting surface 270. The sensor 212 is used to detect the relative heights of the pawl 202 and the bracket pawl 206, as previously described.

In the embodiment shown in FIGS. 17A and 17B, the pawl 202 and the bracket pawl 206 are held on the detecting surface 270 by the force of gravity. The embodiment of the apparatus shown in FIGS. 17A and 17B is therefore suitable for sampling the top of the detecting surface 270, but generally not the side or the bottom of the detecting surface 270, because gravity will not hold the pawl 202 and the bracket pawl 206 against the side or bottom of the detecting surface 270.

The embodiment shown in FIGS. 18A and 18B is similar to the embodiment shown in FIGS. 17A and 17B, with the exception that the bracket pawl 206 and the pawl 202 are mounted on separate pivots 260 as connectors. The embodiment shown in FIGS. 18A and 18B is useful for measuring the top of the detecting surface 270 and is not generally suitable for measuring the side or bottom of the detecting surface 270, because the embodiment depends on gravity to hold the bracket pawl 206 and pawl 202 in contact with the detecting surface 270. Both the embodiment shown in FIGS. 17A and 17B and the embodiment shown in FIGS. 18A and 18B may be utilized in measuring detecting surfaces 170 which are tilted, where the force of gravity is sufficient to hold the bottom of the bracket pawl 206 and the pawl tongue 208 in contact with the detecting surface 270.

FIG. 19 shows an alternative embodiment of a portion of an apparatus in accordance with the present invention in which the pawl 202 and bracket pawl 206 are mounted in a support 274 as a connector. The sensor 212 is mounted on the bracket pawl 206, as in the other embodiments. Springs 276 are located between the support 274 and both the pawl 202 and the bracket pawl 206. The springs 276 push the pawl 202 and the bracket pawl 206 against the detecting surface 270. The embodiment shown in FIG. 19 can therefore be used to measure the bottom and side of the detecting surface 270, because the apparatus of FIG. 19 does not depend on gravity to maintain the pawl 202 and bracket pawl 206 on the detecting surface 270. The springs 276 push the pawl 202 and the bracket pawl 206 against the detecting surface 270. The apparatus shown in FIG. 19 may, of course, also be used to measure the top of the detecting surface 270. A hydraulic mechanism or a pneumatic mechanism may be used in place of the springs 276. The sensor 212 measures the difference between the position of the pawl 202 and the bracket pawl 206, as in the other embodiments. In the embodiment of FIG. 19, the pawl 202 and the bracket pawl 206 both move laterally rather than rotationally, and the pawl 202 and the bracket pawl 206 ride on the detecting surface 270 regardless of the orientation of the detecting surface 270.

Figure 20:
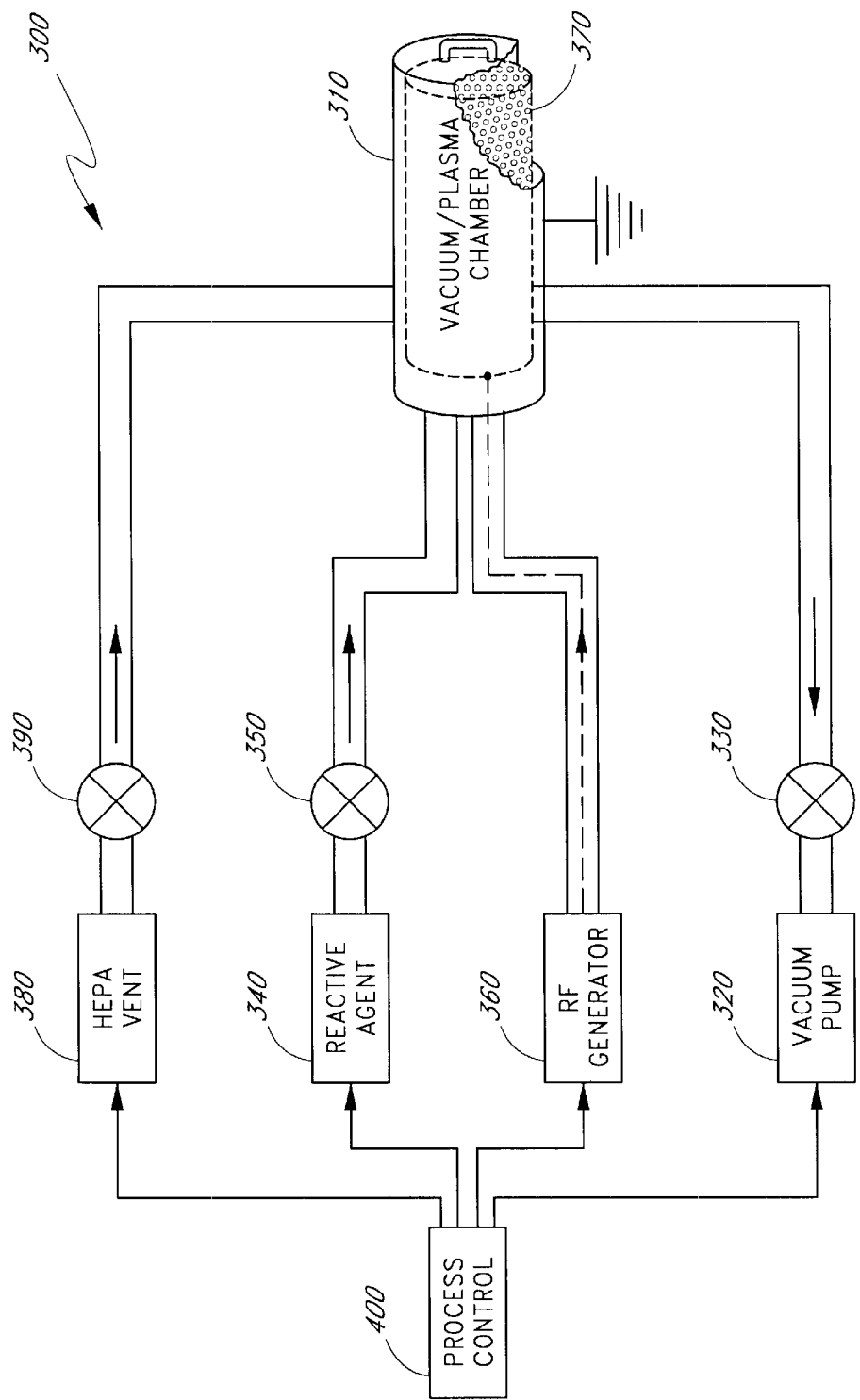
FIG. 20 is a simplified diagram of a sterilization apparatus.

FIG. 20 shows a simplified diagram of a sterilizer 300 suitable for use with the automatic cassette extraction mechanism 160 and the cassette sensing mechanism according to embodiments of the present invention. The sterilizer 300, its components, and methods of use are described more fully in U.S. Pat. No. 4,756,882, issued Jul. 12, 1988, and U.S. Pat. No. 5,656,238, issued Aug. 12, 1997, herein incorporated by reference. Other sterilizers are suitable for use with the automatic cassette extraction mechanism 160 and the cassette sensing mechanism, and the sterilizer of FIG. 20 is not meant to be limiting. The sterilizer 300 includes a vacuum chamber 310, a vacuum pump 320 connected to the vacuum chamber 310 by a valve 330, and a source of suitable sterilant 340 such as hydrogen peroxide connected to the vacuum chamber 310 by a line having a valve 350 therein. The sterilizer 300 also includes an RF generator 360 electrically connected to the plasma generator 370 inside the vacuum chamber 310 as well as a HEPA vent 380 connected to the vacuum chamber 310 via a line and a valve 390. A process control logic 400, preferably a programmable computer, is connected to each of the components which are connected to the vacuum chamber 310. The process control logic 400 directs the operation of each of the components connected to the vacuum chamber 310 at the appropriate time to effectuate the sterilization process.

The automatic cassette extraction mechanism 160 and the cassette sensing mechanism of various embodiments of the present invention are portions of an embodiment of the source of suitable sterilant 340, and both the automatic cassette extraction mechanism 160 and the cassette sensing mechanism may be controlled by the process control logic 400. The vacuum chamber 310 contains the objects to be sterilized.

While embodiments and applications of this invention have been shown and described, it should be evident to those skilled in the art that many more modifications are possible without departing from the scope of the invention. The invention is therefore not to be restricted, except in the spirit of the appended claims.

What is claimed is:

1. A sensing mechanism for detecting an unevenness of a surface on a device, wherein said surface has at least a first path and a second path therealong, wherein said first path and said second path are noncoincident, said mechanism comprising:

at least one connector;

a first pawl, wherein a first end of said first pawl is connected to said connector in a manner allowing movement of said first pawl and wherein a second end of said first pawl contacts a portion of said first path on said surface;

a second pawl, wherein a first end of said second pawl is connected to said connector in a manner allowing movement of said second pawl and wherein a second end of said second pawl contacts a portion of said second path; and a sensor mounted on said first pawl or said second pawl, wherein said sensor detects a position of said first pawl relative to said second pawl.

2. The sensing mechanism of claim 1, wherein said first path is adjacent said second path.

3. The sensing mechanism of claim 1, wherein said at least one connector is a pivot and wherein said first pawl and said second pawl rotate about said pivot.

4. The sensing mechanism of claim 1, wherein the movement of said first pawl and said second pawl is due to gravity.

5. The sensing mechanism of claim 1, wherein the movement of said first pawl and said second pawl is due to a moving mechanism comprising at least one spring.

6. The sensing mechanism of claim 1, wherein said unevenness of said surface is on the top, bottom, or side of said device.

7. The sensing mechanism of claim 1, wherein said sensor comprises a photoelectric sensor.

8. The sensing mechanism of claim 1, further comprising a control unit.

9. The sensing mechanism of claim 1, wherein said device is a cassette.

10. The sensing mechanism of claim 9, wherein said cassette contains germicide.

11. The sensing mechanism of claim 10, wherein the germicide comprises hydrogen peroxide.

12. The sensing mechanism of claim 1, wherein said first path has at least one groove and said second path is relatively smooth.

13. The sensing mechanism of claim 12, wherein said first path and said second path are on a surface of a cassette.

14. A sensing mechanism for detecting an unevenness of a surface on a device, wherein said surface has at least a first path and a second path therealong, wherein said device is a cassette, said mechanism comprising:
  at least one connector;
  a first pawl, wherein a first end of said first pawl is connected to said connector in a manner allowing movement of said first pawl and wherein a second end of said first pawl contacts a portion of said first path on said surface;
  a second pawl, wherein a first end of said second pawl is connected to said connector in a manner allowing movement of said second pawl and wherein a second end of said second pawl contacts a portion of said second path; and
  a sensor mounted on said first pawl or said second pawl, wherein said sensor detects a position of said first pawl relative to said second pawl.

15. The sensing mechanism of claim 14, wherein said cassette contains germicide.

16. The sensing mechanism of claim 15, wherein the germicide comprises hydrogen peroxide.

17. A sensing mechanism for detecting an unevenness of a surface on a device, wherein said surface has at least a first path and a second path therealong, wherein said first path has at least one groove and said second path is relatively smooth, said mechanism comprising:
  at least one connector;
  a first pawl, wherein a first end of said first pawl is connected to said connector in a manner allowing movement of said first pawl and wherein a second end of said first pawl contacts a portion of said first path on said surface;
  a second pawl, wherein a first end of said second pawl is connected to said connector in a manner allowing movement of said second pawl and wherein a second end of said second pawl contacts a portion of said second path; and
  a sensor mounted on said first pawl or said second pawl, wherein said sensor detects a position of said first pawl relative to said second pawl.

18. The sensing mechanism of claim 17, wherein said first path and said second path are on a surface of a cassette.

19. A method for sensing an unevenness of a surface on a device, said method comprising:
  providing a device having a surface, wherein said surface has a first path and a second path therealong;
  providing a sensing mechanism, said mechanism comprising:
    at least one connector;
    a first pawl, wherein a first end of said first pawl is connected to said connector in a manner allowing movement of said first pawl;
    a second pawl, wherein a first end of said second pawl is connected to said connector in a manner allowing movement of said second pawl; and
    a sensor mounted on said first pawl or said second pawl;
  inserting said device into said sensing mechanism, wherein a second end of said first pawl contacts a portion of said first path on said surface of said device and wherein a second end of said second pawl contacts a portion of said second path on said surface of said device;
  determining a position of said first pawl relative to said second pawl with said sensor;
  moving said device in said sensing mechanism;
  determining a second position of said first pawl relative to said second pawl with said sensor;
  determining an unevenness of said surface; and
  repeating the steps of moving said device and determining the position of said first pawl relative to said second pawl.

20. A method for sensing an unevenness of a surface on a device, said method comprising:
  providing a device having a surface, wherein said surface has a first path and a second path therealong, wherein said first and said second path are noncoincident;
  providing a sensing mechanism, said mechanism comprising:
    at least one connector;
    a first pawl, wherein a first end of said first pawl is connected to said connector in a manner allowing movement of said first pawl;
    a second pawl, wherein a first end of said second pawl is connected to said connector in a manner allowing movement of said second pawl; and
    a sensor mounted on said first pawl or said second pawl;
  inserting said device into said sensing mechanism, wherein a second end of said first pawl contacts a portion of said first path on said surface of said device and wherein a second end of said second pawl contacts a portion of said second path on said surface of said device;
  determining a position of said first pawl relative to said second pawl with said sensor;
  moving said device in said sensing mechanism;
  determining a second position of said first pawl relative to said second pawl with said sensor; and
  determining an unevenness of said surface.

21. The method of claim 20, wherein said first path is adjacent said second path.

22. The method of claim 20, further comprising repeating the steps of moving said device and determining the position of said first pawl relative to said second pawl.

23. The method of claim 20, wherein said at least one connector is a pivot and wherein said first pawl and said second pawl rotate about said pivot.

24. The method of claim 20, wherein said sensor comprises a photoelectric sensor.

25. The method of claim 20, wherein said sensing mechanism further comprises a control unit.

26. The method of claim 20, wherein said device is a cassette.

27. The method of claim 26, wherein said sensing mechanism is comprised in a sterilization system.

28. The method of claim 27, wherein said cassette contains germicide.

29. The method of claim 28, wherein the germicide comprises hydrogen peroxide.

30. The method of claim 28, wherein said first path has at least one groove and said second path is relatively smooth.

31. The method of claim 30, further comprising moving said cassette until said second end of said first pawl contacts said at least one groove in said first path on said surface of said cassette, thereby positioning said cassette for injection of germicide into said sterilization system.

32. The method of claim 31, further comprising injecting said germicide into said sterilization system.

33. A method for sensing an unevenness of a surface on a device, wherein said device is a cassette, said method comprising:

providing a device having a surface, wherein said surface has a first path and a second path therealong;

providing a sensing mechanism, said mechanism comprising:

at least one connector;

a first pawl, wherein a first end of said first pawl is connected to said connector in a manner allowing movement of said first pawl;

a second pawl, wherein a first end of said second pawl is connected to said connector in a manner allowing movement of said second pawl; and a sensor mounted on said first pawl or said second pawl;

inserting said device into said sensing mechanism, wherein a second end of said first pawl contacts a portion of said first path on said surface of said device and wherein a second end of said second pawl contacts a portion of said second path on said surface of said device;

determining a position of said first pawl relative to said second pawl with said sensor;

moving said device in said sensing mechanism;

determining a second position of said first pawl relative to said second pawl with said sensor; and determining an unevenness of said surface.

34. The method of claim 33, wherein said sensing mechanism is comprised in a sterilization system.

35. The method of claim 34, wherein said cassette contains germicide.

36. The method of claim 35, wherein the germicide comprises hydrogen peroxide.

37. The method of claim 35, wherein said first path has at least one groove and said second path is relatively smooth.

38. The method of claim 37, further comprising moving said cassette until said second end of said first pawl contacts said at least one groove in said first path on said surface of said cassette, thereby positioning said cassette for injection of germicide into said sterilization system.

39. The method of claim 38, further comprising injecting said germicide into said sterilization system.

* * * * *